(12) United States Patent
Kano

(10) Patent No.: US 9,184,370 B2
(45) Date of Patent: Nov. 10, 2015

(54) ULTRASONIC TRANSDUCER DEVICE, ULTRASONIC MEASUREMENT APPARATUS, HEAD UNIT, PROBE, AND ULTRASONIC IMAGING APPARATUS

(71) Applicant: SEIKO EPSON CORPORATION, Tokyo (JP)

(72) Inventor: Kazuyuki Kano, Aichi (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/190,421

(22) Filed: Feb. 26, 2014

(65) Prior Publication Data
US 2014/0241112 A1 Aug. 28, 2014

(30) Foreign Application Priority Data

Feb. 28, 2013 (JP) ................................. 2013-038456

(51) Int. Cl.
H01L 41/00 (2013.01)
H01L 41/047 (2006.01)
H01L 41/09 (2006.01)
G01S 7/56 (2006.01)
G01S 15/02 (2006.01)
B06B 1/02 (2006.01)
B06B 1/06 (2006.01)

(52) U.S. Cl.
CPC .......... H01L 41/0475 (2013.01); B06B 1/0207 (2013.01); B06B 1/0622 (2013.01); B06B 1/0662 (2013.01); G01S 7/56 (2013.01); G01S 15/02 (2013.01); H01L 41/09 (2013.01)

(58) Field of Classification Search
CPC ............ H04B 11/00; H04B 1/16; B06B 1/06; B06B 1/0207; B06B 1/0688; B06B 1/0644; H01L 41/0475; H01L 41/09; G01S 7/56
USPC .......................................................... 367/135
See application file for complete search history.

(56) References Cited

U.S. PATENT DOCUMENTS

| 4,412,316 | A | * | 10/1983 | Diepers | 367/105 |
| 5,864,262 | A | * | 1/1999 | Ikada | 333/193 |
| 6,344,705 | B1 | * | 2/2002 | Solal et al. | 310/313 B |
| 6,407,484 | B1 | * | 6/2002 | Oliver et al. | 310/339 |
| 2002/0105250 | A1 | * | 8/2002 | Klee et al. | 310/365 |

(Continued)

FOREIGN PATENT DOCUMENTS

| EP | 1629778 A1 | 3/2006 |
| JP | 2006-061252 A | 3/2006 |

(Continued)

Primary Examiner — Isam Alsomiri
Assistant Examiner — Hovhannes Baghdasaryan
(74) Attorney, Agent, or Firm — Global IP Counselors, LLP

(57) ABSTRACT

An ultrasonic transducer device includes an ultrasonic element array and a common electrode wiring. The ultrasonic element array has three ultrasonic element rows with each of the three ultrasonic element rows including a plurality of ultrasonic elements arranged along a first direction and electrically connected to each other. The three ultrasonic element rows are arranged along a second direction intersecting with the first direction. The common electrode wiring is configured and arranged to supply a common voltage to at least one of the three ultrasonic element rows. The common electrode wiring extends in the first direction and is arranged between two of the three ultrasonic element rows positioned on outer sides among the three ultrasonic element rows with respect to the second direction.

17 Claims, 16 Drawing Sheets

(56) References Cited

U.S. PATENT DOCUMENTS

| | | | |
|---|---|---|---|
| 2004/0130411 A1* | 7/2004 | Beaudin et al. | 333/133 |
| 2005/0165314 A1* | 7/2005 | Tanaka | 600/459 |
| 2008/0002375 A1* | 1/2008 | Nozaki et al. | 361/749 |
| 2008/0027323 A1* | 1/2008 | Freiburger | 600/453 |
| 2008/0172051 A1* | 7/2008 | Masuda et al. | 606/37 |
| 2009/0230822 A1* | 9/2009 | Kushculey et al. | 310/366 |
| 2009/0240151 A1* | 9/2009 | Sabata | 600/447 |
| 2009/0318808 A1* | 12/2009 | Brader | 600/443 |
| 2010/0189288 A1* | 7/2010 | Menzel et al. | 381/151 |
| 2010/0292632 A1* | 11/2010 | Mulvihill et al. | 604/22 |
| 2011/0127881 A1* | 6/2011 | Howarth | 310/319 |
| 2011/0237974 A1* | 9/2011 | Bartol et al. | 600/554 |
| 2011/0263982 A1 | 10/2011 | Kano | |
| 2012/0123263 A1* | 5/2012 | Osaka et al. | 600/438 |
| 2012/0188849 A1 | 7/2012 | Matsuda et al. | |
| 2013/0226005 A1 | 8/2013 | Kano | |

FOREIGN PATENT DOCUMENTS

| | | |
|---|---|---|
| JP | 2007-142555 A | 6/2007 |
| JP | 2011-234073 A | 11/2011 |
| JP | 2012-152319 A | 8/2012 |
| JP | 2013-055978 A | 3/2013 |
| JP | 2013-172799 A | 9/2013 |

* cited by examiner

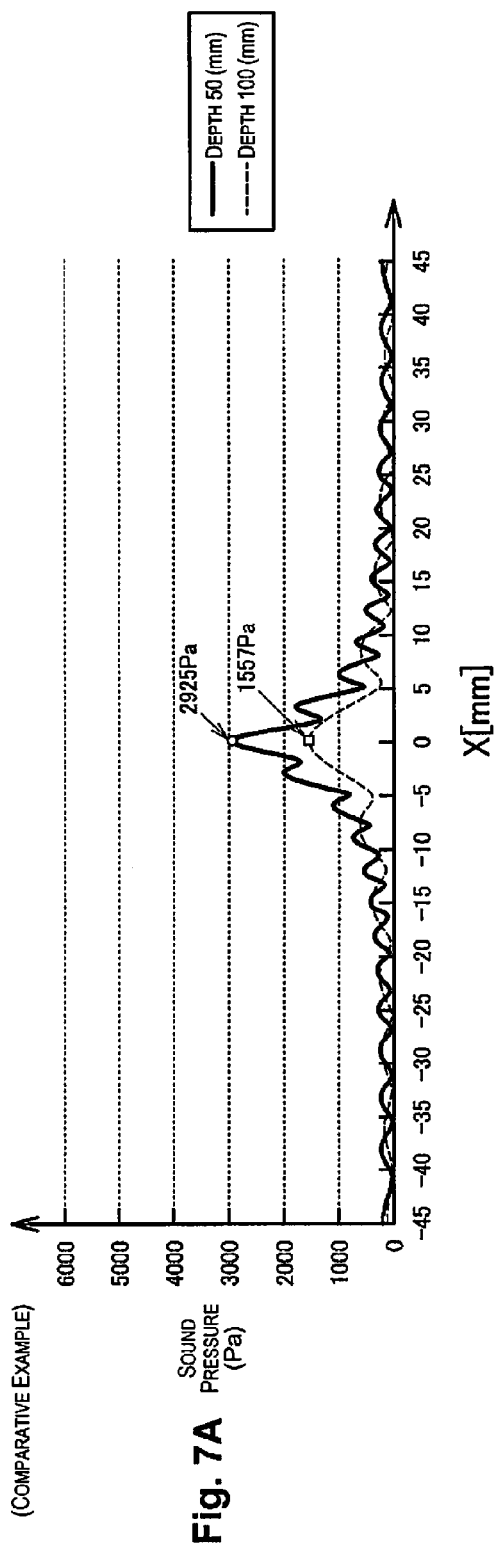
Fig. 7A (Comparative Example)
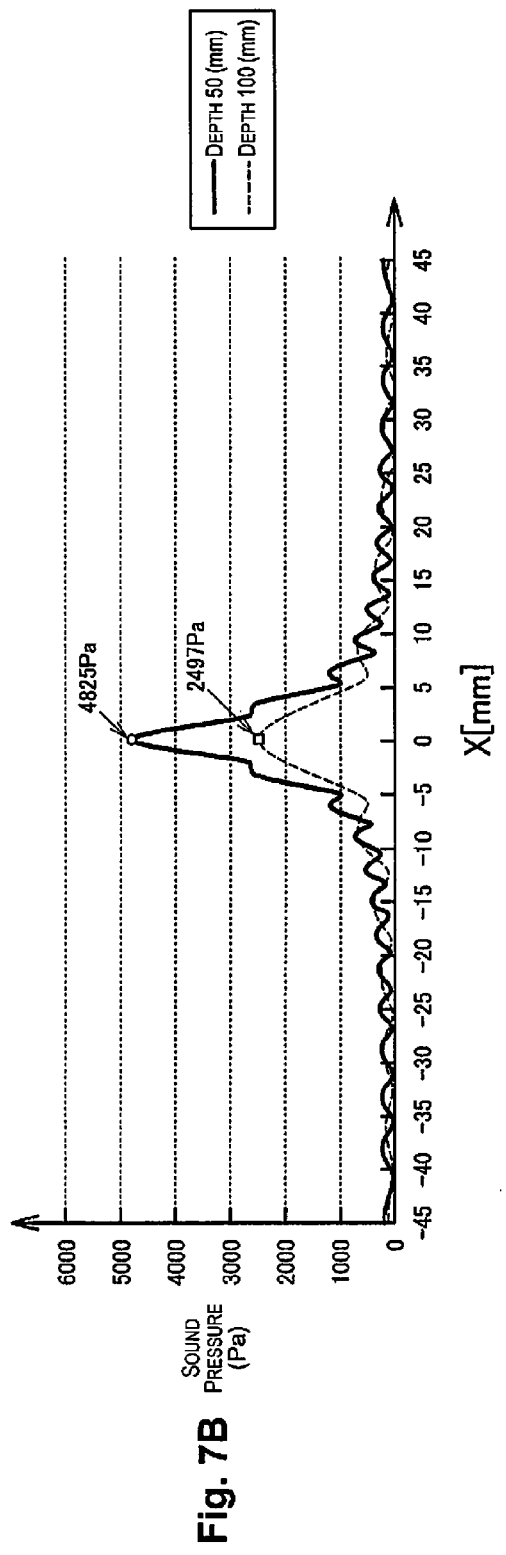
Fig. 7B

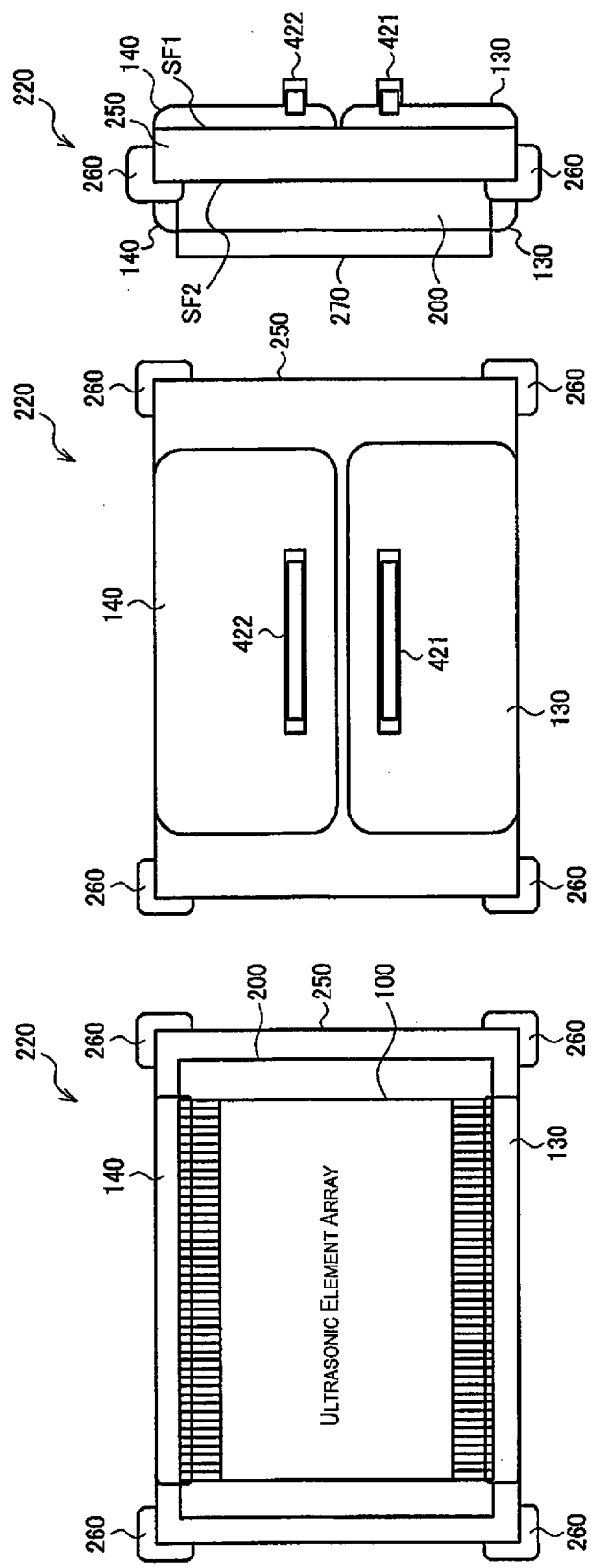

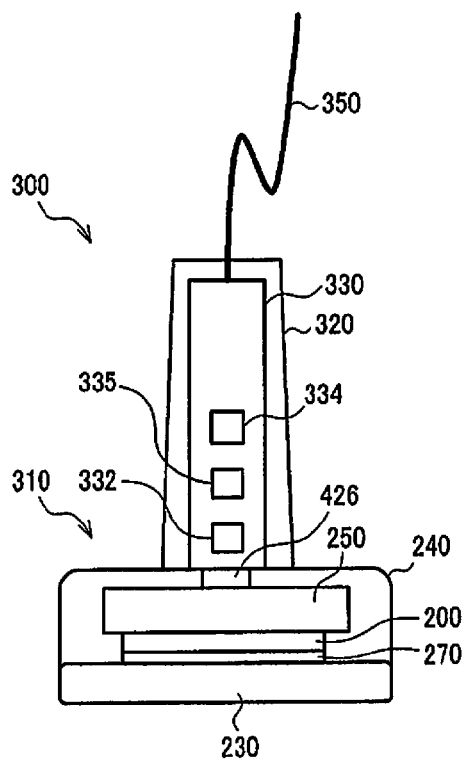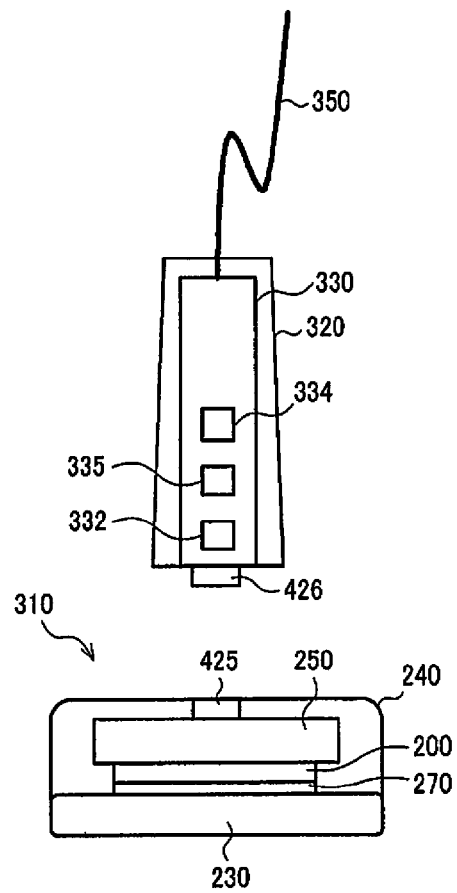
Fig. 15A
Fig. 15B

ULTRASONIC TRANSDUCER DEVICE, ULTRASONIC MEASUREMENT APPARATUS, HEAD UNIT, PROBE, AND ULTRASONIC IMAGING APPARATUS

CROSS-REFERENCE TO RELATED APPLICATIONS

This application claims priority to Japanese Patent Application No. 2013-038456 filed on Feb. 28, 2013. The entire disclosure of Japanese Patent Application No. 2013-038456 is hereby incorporated herein by reference.

BACKGROUND

1. Technical Field

The present invention relates to an ultrasonic transducer device, an ultrasonic measurement apparatus, a head unit, a probe, an ultrasonic imaging apparatus, and the like.

2. Related Art

An ultrasonic apparatus is known which emits ultrasonic waves from a front end of a probe toward a target object and detects ultrasonic waves which are reflected from the target object (for example, Japanese Unexamined Patent Application Publication No. 2007-142555). For example, the ultrasonic apparatus is used as an ultrasonic imaging apparatus which is used in diagnosis by imaging inside the body of a patient or the like. For example, a piezoelectric element is used as an ultrasonic element which emits ultrasonic waves.

SUMMARY

A voltage amplitude which is applied to the piezoelectric element is determined with a potential of a common electrode of the ultrasonic element as a reference. In the prior art, since common electrode wiring which is shared is connected with respect to all of the ultrasonic elements, impedance of the common electrode wiring is higher with the ultrasonic elements which are farther from a common terminal which supplies the common voltage. As a result, there is a problem in that the potential of the common electrode varies according to a driving signal with the ultrasonic elements which are farther from the common terminal and the voltage amplitude which is actually applied to the ultrasonic elements is smaller.

According to several aspects of the present invention, it is possible to provide an ultrasonic transducer device, an ultrasonic measurement apparatus, a head unit, a probe, an ultrasonic imaging apparatus, and the like which are able to suppress a reduction in voltage amplitude which is applied to an ultrasonic element.

An ultrasonic transducer device according to one aspect includes an ultrasonic element array and a common electrode wiring. The ultrasonic element array has three ultrasonic element rows with each of the three ultrasonic element rows including a plurality of ultrasonic elements arranged along a first direction and electrically connected to each other. The three ultrasonic element rows are arranged along a second direction intersecting with the first direction. The common electrode wiring is configured and arranged to supply a common voltage to at least one of the three ultrasonic element rows. The common electrode wiring extends in the first direction and is arranged between two of the three ultrasonic element rows positioned on outer sides among the three ultrasonic element rows with respect to the second direction.

According to this aspect, the common electrode wiring which supplies the common voltage to the one row of the ultrasonic element rows out of the three rows of the ultrasonic element rows is arranged between two rows of the ultrasonic element rows which are positioned on the outer sides out of the three rows of the ultrasonic element rows. Due to this, it is possible to suppress a reduction in voltage amplitude which is applied to the ultrasonic elements.

In addition, in another aspect, the ultrasonic element array preferably has a $1^{st}$ to an $n^{th}$ ultrasonic element rows (where n is an integer of three or more) including the three ultrasonic element rows with the $1^{st}$ to the $n^{th}$ ultrasonic element rows being arranged along the second direction, and the common electrode wiring is preferably configured and arranged to supply the common voltage to an $i^{th}$ to a $j^{th}$ ultrasonic element rows (where i and j are natural numbers such that $i \leq j \leq n-1$) among the $1^{st}$ to the $n^{th}$ ultrasonic element rows, and is arranged between a $k^{th}$ ultrasonic element row and a $k+1^{th}$ ultrasonic element row (where k is a natural number such that $i-1 \leq k \leq j$) among an to the $i^{th}$ ultrasonic element rows.

By doing so, it is possible to arrange the common electrode wiring, which supplies the common voltage to the $i^{th}$ to the $i^{th}$ of the ultrasonic element rows, between the $k^{th}$ of the ultrasonic element rows and the $k+1^{th}$ of the ultrasonic element rows out of the to the $j^{th}$ of the ultrasonic element rows. Due to this, it is possible to supply the common voltage with a low resistance with respect to the $i^{th}$ to the $j^{th}$ of the ultrasonic element rows and it is possible to suppress a reduction in voltage amplitude which is applied to the ultrasonic elements.

In addition, in another aspect, the ultrasonic transducer device preferably further includes: a substrate on which the ultrasonic element array and the common electrode wiring are arranged; and a signal electrode wiring disposed on the substrate and configured and arranged to perform at least one of supplying and receiving of signals with respect to at least one of the three ultrasonic element rows. Each of the ultrasonic elements in the at least one of the three ultrasonic element rows preferably has a first electrode, a second electrode, and a transducer section arranged between the first electrode and the second electrode, with the first electrode being connected to the signal electrode wiring, and the second electrode being connected to the common electrode wiring.

There is a possibility that wiring resistance may be generated in the common electrode wiring in a case where the common electrode wiring is formed on the substrate, but according to the aspect of the present invention, it is possible to supply the common voltage with low resistance even in such a case and it is possible to suppress a reduction in voltage amplitude which is applied to the ultrasonic elements.

In addition, in another aspect, the substrate preferably has a plurality of openings arranged in an array formation. Each of the ultrasonic elements preferably has a vibrating film covering a corresponding one of the openings and a piezoelectric element section disposed on the vibrating film. The piezoelectric element section preferably has a lower electrode disposed on the vibrating film as one of the first electrode and the second electrode, a piezoelectric body layer as the transducer section covering at least a portion of the lower electrode, and an upper electrode as the other of the first electrode and the second electrode covering at least a portion of the piezoelectric body layer.

By doing so, it is possible to configure the ultrasonic element array using the ultrasonic elements where the vibrating films which block off the openings vibrate due to the piezoelectric elements. Due to this, it is possible to drive the ultrasonic elements using a driving signal with a low voltage compared to a case where bulk piezoelectric elements are used and it is possible to form a transmission circuit in a compact manner since it is possible to manufacture the transmission circuit in a process with a low resistance to voltage.

In addition, in another aspect, the ultrasonic transducer device preferably further includes: a plurality of signal electrode wirings; a first common electrode wiring as the common electrode wiring; and at least a second and a third common electrode wirings. The ultrasonic element array preferably has a plurality of ultrasonic element rows including the three ultrasonic element rows. Each of the signal electrode wirings preferably extends in the first direction and configured and arranged to perform at least one of supplying and receiving of signals with respect to at least one of the ultrasonic element rows. Each of the first to third common electrode wirings preferably extends in the first direction and configured and arranged to supply the common voltage with respect to at least one of the ultrasonic element rows.

By doing so, at least the first common electrode wiring is arranged between the ultrasonic element rows and it is possible to supply the common voltage to each of one or a plurality of the ultrasonic element rows using the first to the third common electrode wirings. Due to this, it is possible to suppress a reduction in voltage amplitude which is applied to the ultrasonic elements since it is possible for wiring resistance from the common electrode wiring to the ultrasonic elements to be smaller.

In addition, in another aspect, the first common electrode wiring is preferably electrically connected to a $1^{st}$ to a $p^{th}$ ultrasonic element rows (where p is a natural number) among the ultrasonic element rows and is electrically not connected to a $p+1^{th}$ to a $q^{th}$ ultrasonic element rows (where q is a natural number such that q>p) among the ultrasonic element rows. The second common electrode wiring is preferably electrically connected to the $p+1^{th}$ to the $q^{th}$ ultrasonic element rows and electrically not connected to the $1^{st}$ to the $p^{th}$ ultrasonic element rows.

By doing so, it is possible to suppress crosstalk between the ultrasonic element rows via variation in voltage in the common electrode wiring since it is possible for the common electrode wiring which is connected to the $1^{st}$ to the $p^{th}$ of the ultrasonic element rows and the common electrode wiring which is connected to the $p+1^{th}$ to the $q^{th}$ of the ultrasonic element rows to be electrically not connected.

In addition, in another aspect, the ultrasonic transducer device preferably further includes: a first end signal terminal arranged at a first end of the ultrasonic element array in the first direction and is connected to a first end of at least one of the signal electrode wirings; and a second end signal terminal arranged at a second end of the ultrasonic element array in the first direction and is connected to a second end of the at least one of the signal electrode wirings.

In addition, in another aspect, the ultrasonic transducer device preferably further includes: a first end common terminal arranged at a first end of the ultrasonic element array in the first direction and is connected to a first end of at least one of the first to the third common electrode wirings; and a second end common terminal arranged at a second end of the ultrasonic element array in the first direction and is connected to a second end of the at least one of the first to third common electrode wirings.

According to these aspects, it is possible to have attenuation of voltage amplitude which is applied between the electrodes of the ultrasonic elements be symmetrical from both ends of the ultrasonic element rows toward the center since it is possible to supply the driving signal and the common voltage from both ends of the ultrasonic element rows. That is, it is possible to suppress a sound field from becoming unsymmetrical with attenuation of voltage amplitude from the first end side of the ultrasonic element rows toward the second end side.

In addition, in another aspect, the ultrasonic transducer device preferably further includes: a first common terminal connected with the first common electrode wiring; a second common terminal connected with the second common electrode wiring; a first signal terminal connected in common with a $1^{st}$ to an $r^{th}$ signal electrode wirings (where r is a natural number) among the signal electrode wirings; and a second signal terminal connected in common with a $r+1^{th}$ to a $2r^{th}$ signal electrode wirings among the signal electrode wirings. The first common electrode wiring and the $1^{st}$ to the $r^{th}$ signal electrode wirings are preferably electrically connected to a $1^{st}$ to an $r^{th}$ ultrasonic element rows among the ultrasonic element rows. The second common electrode wiring and the $r+1^{th}$ to the $2r^{th}$ signal electrode wirings are preferably electrically connected to an $r+1^{th}$ to a $2r^{th}$ ultrasonic element rows among the ultrasonic element rows.

By doing this, it is possible to suppress crosstalk between channels via variation in voltage in the common electrode wirings since it is possible to separate the common electrode wirings for each channel which performs at least one of transmitting and receiving of signals.

In addition, in another aspect, the signal electrode wiring preferably extends in the first direction at a position overlapping with the transducer section in a plan view with respect to the ultrasonic element arrays, and the common electrode wiring preferably extends in the first direction at a position which does not overlap with the transducer section in the plan view.

By doing this, it is possible to narrow the pitch for arranging the ultrasonic element rows in the second direction since it is possible to arrange the signal electrode wirings below the transducer section. Due to this, it is possible to suppress grating lobes.

In addition, in another aspect, the signal electrode wiring preferably extends in the first direction at a position which does not overlap with the transducer section in a plan view with respect to the ultrasonic element arrays, and the common electrode wiring preferably extends in the first direction at a position which does not overlap with the transducer section and the signal electrode wiring in the plan view.

By doing this, it is possible to determine the width of the signal electrode wirings without limiting the width of the transducer section since it is possible to provide the signal electrode wirings at a position which does not overlap with the transducer section. Due to this, it is possible to reduce wiring impedance in the signal electrode wirings.

An ultrasonic transducer device according to another aspect includes a substrate, an ultrasonic element array, and a common electrode wiring. The ultrasonic element array is arranged in an array formation on the substrate. The ultrasonic element array includes a first ultrasonic element arranged at a corner of the ultrasonic element array and a second ultrasonic element arranged in a center portion of the ultrasonic element array. The common electrode wiring is disposed on the substrate so that a potential of a common electrode in the first ultrasonic element and a potential of a common electrode of the second ultrasonic element are substantially the same.

By doing this, it is possible to configure an ultrasonic transducer device so as to not generate a difference between the common voltage which is supplied to the ultrasonic elements at the corner of the ultrasonic element array, and the common voltage which is supplied to the ultrasonic elements at the center of the ultrasonic element array. Due to this, it is possible to suppress a reduction in voltage amplitude which is applied between the electrodes in the ultrasonic elements at a central section of the ultrasonic element array since disparity in the common voltage at the corner and the center of the ultrasonic element array is small.

In addition, in another aspect, the ultrasonic element array preferably has three ultrasonic element rows with each of the three ultrasonic element rows including a plurality of ultrasonic elements arranged along a first direction and electrically connected to each other, the three ultrasonic element rows being arranged along a second direction intersecting with the first direction. The common electrode wiring is preferably configured and arranged to supply a common voltage to one of the three ultrasonic element rows, the common electrode wiring extending in the first direction and being arranged between two of the three ultrasonic element rows positioned on outer sides among the three ultrasonic element rows with respect to the second direction.

In addition, an ultrasonic measurement apparatus according to another aspect includes an ultrasonic transducer device, a first flexible substrate and a second flexible substrate. The ultrasonic transducer device includes: an ultrasonic element array having three ultrasonic element rows with each of the three ultrasonic element rows including a plurality of ultrasonic elements arranged along a first direction and electrically connected to each other, the three ultrasonic element rows being arranged along a second direction intersecting with the first direction; and a common electrode wiring configured and arranged to supply a common voltage to at least one of the three ultrasonic element rows, the common electrode wiring extending in the first direction and being arranged between two of the three ultrasonic element rows positioned on outer sides among the three ultrasonic element rows with respect to the second direction; a substrate on which the ultrasonic element array and the common electrode wiring are arranged; and three signal electrode wirings disposed on the substrate and configured and arranged to perform at least one of supplying and receiving of signals with respect to corresponding ones of the three ultrasonic element rows. The first flexible substrate includes a plurality of first signal wirings. The second flexible wiring includes a plurality of second signal wirings. Three of the first signal wirings are respectively connected to first ends of the three signal electrode wirings. Three of the second signal wirings are respectively connected to second ends of the three signal electrode wirings.

In addition, in another aspect, the ultrasonic measurement apparatus preferably further includes: a first integrated circuit device mounted on the first flexible substrate and has a plurality of first transmission circuits; and a second integrated circuit device mounted on the second flexible substrate and has a plurality of second transmission circuits. Each of the first transmission circuits is configured and arranged to output a transmission signal to a corresponding one of the first signal wirings. Each of the second transmission circuits is configured and arranged to output a transmission signal to a corresponding one of the second signal wirings.

In addition, a head unit of a probe according to another aspect includes the ultrasonic transducer device according to any one of the above described aspects. The ultrasonic transducer device is configured and arranged to be attached and detached with respect to a probe body of the probe.

In addition, a probe according to another aspect includes: the ultrasonic transducer device according to any one of the above described aspects; and a probe body.

In addition, an ultrasonic imaging apparatus according to another aspect includes: the ultrasonic transducer device according to any one of the above described aspects; and a display section configured and arranged to display image data.

BRIEF DESCRIPTION OF THE DRAWINGS

Referring now to the attached drawings which form a part of this original disclosure:

FIG. 7A is a characteristic example of distribution of radiated sound pressure in a comparative example and FIG. 7B is a characteristic example of distribution of radiated sound pressure in an embodiment.

FIGS. 14A to 14C are detailed configuration examples of a head unit.

FIGS. 15A and 15B are configuration examples of an ultrasonic probe.

DETAILED DESCRIPTION OF EXEMPLARY EMBODIMENTS

The following describes a preferred embodiment of the present invention in detail. Here, the present embodiment described below is not gratuitously limited by the content of the present invention described in the scope of the claims and the entire configuration described in the present embodiment is not necessarily essential as a means to solve the problems in the present invention.

1. Ultrasonic Element

Figure 1A:
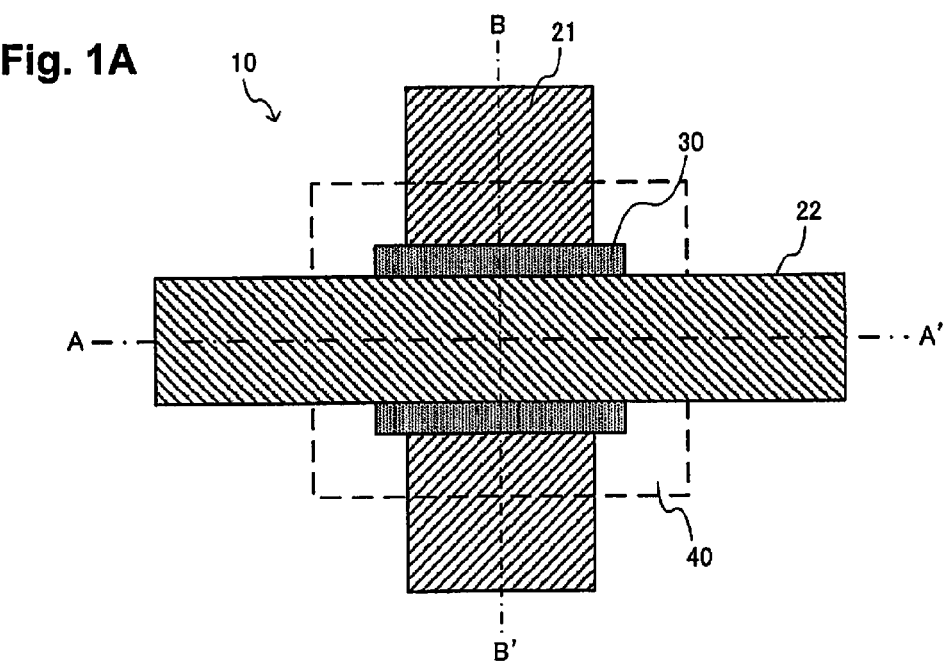
FIGS. 1A to 1C are configuration examples of an ultrasonic element.
Figure 1B:
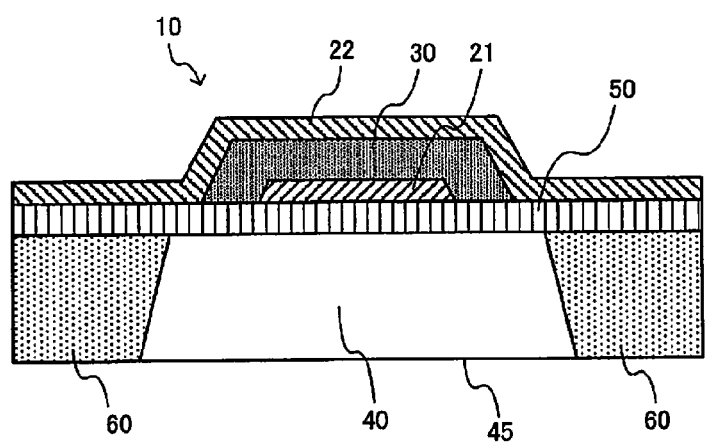
Figure 1C:
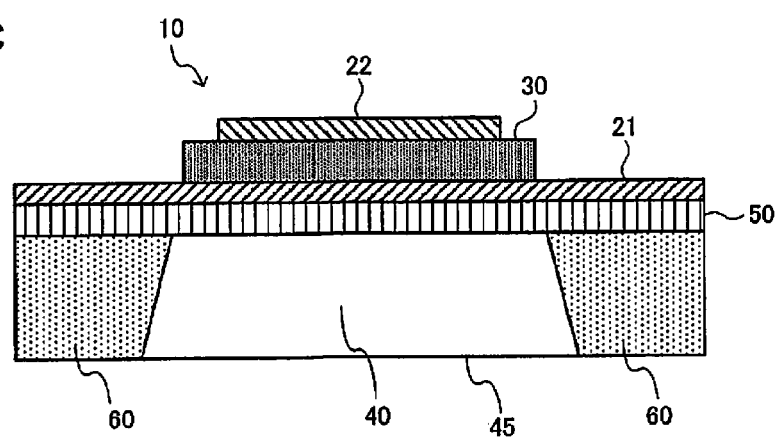

FIGS. 1A to 1C illustrate a configuration example of an ultrasonic element 10 which is applied to an ultrasonic transducer device of the present embodiment. The ultrasonic element 10 (an ultrasonic transducer element) has a vibrating film 50 (a membrane and a support member), and a piezoelectric element section. The piezoelectric element section has a first electrode layer 21 (a lower electrode), a piezoelectric body layer 30 (a piezoelectric body film), and a second electrode layer 22 (an upper electrode).

FIG. 1A is a planar diagram of the ultrasonic element 10 which is formed on a substrate 60 (a silicon substrate) viewed from a direction which is orthogonal to the substrate on an element forming surface side. FIG. 1B is a cross sectional diagram illustrating a cross section along AA' in FIG. 1A. FIG. 1C is a cross sectional diagram illustrating a cross section along BB' in FIG. 1A.

The first electrode layer 21 is formed by, for example, a metal thin film on an upper layer of the vibrating film 50. The first electrode layer 21 may be wiring which extends to an outer side of an element forming region as shown in FIG. 1A and is connected to the adjacent ultrasonic element 10.

The piezoelectric body layer 30 is formed using, for example, a PZT (lead zirconate titanate) thin film and is provided so as to cover at least a portion of the first electrode layer 21. Here, the material of the piezoelectric body layer 30 is not limited to PZT, and for example, lead titanate ($PbTiO_3$), lead zirconate ($PbZrO_3$), lanthanum-modified lead titanate ($(Pb, La)TiO_3$), and the like may be used.

The second electrode layer 22 is formed using, for example, a thin metal film and is provided so as to cover at least a portion of the piezoelectric body layer 30. The second electrode layer 22 may be wiring which extends to an outer side of the element forming region as shown in FIG. 1A and is connected to the adjacent ultrasonic element 10.

The vibrating film 50 (the membrane) is provided so as to block off an opening 40 using a two layer structure of, for example, an $SiO_2$ thin film and a $ZrO_2$ thin film. It is possible for the vibrating film 50 to support the piezoelectric body layer 30, the first electrode layer 21, and the second electrode layer 22, to vibrate according to expansions and contractions of the piezoelectric body layer 30, and to generate ultrasonic waves.

The opening 40 (a hollow region) is formed by etching using reactive ion etching (RIE) or the like from the rear surface (the surface where elements are not formed) side of the substrate 60. The resonance frequency of the ultrasonic waves is determined by the size of the vibrating film 50 which is able to vibrate according to the forming of the opening 40 and the ultrasonic waves are radiated to the piezoelectric body layer 30 side (in a forward direction from behind the surface of the diagram in FIG. 1A).

A first electrode of the ultrasonic element 10 is formed using one out of the first electrode layer 21 and the second electrode layer 22 and a second electrode is formed using the other out of the first electrode layer 21 and the second electrode layer 22. In detail, one out of a portion which is covered by the piezoelectric body layer 30 out of the first electrode layer 21 and a portion which covers the piezoelectric body layer 30 out of the second electrode layer 22 forms the first electrode and the other portion of the first electrode layer 21 and the second electrode layer 22 forms the second electrode. That is, the piezoelectric body layer 30 is provided to interpose the first electrode and the second electrode.

The piezoelectric layer body 30 expands and contracts in an in-plane direction due to a voltage being applied between the first electrode and the second electrode, that is, between the first electrode layer 21 and the second electrode layer 22. The ultrasonic element 10 uses a monomorphic (unimorphic) structure where a thin piezoelectric element (the piezoelectric body layer 30) and a metal plate (the vibrating film 50) are bonded, and warping is generated in order to maintain the dimensions of the vibrating film 50 which is bonded to the piezoelectric body layer 30 when the piezoelectric body layer 30 expands and contracts in the plane. The vibrating film 50 vibrates with respect to a film thickness direction due to an alternating current being applied to the piezoelectric body layer 30, and ultrasonic waves are radiated due to the vibration of the vibrating film 50. The voltage which is applied to the piezoelectric body layer 30 is, for example, 10 to 30 V and the frequency is, for example, 1 to 10 MHz.

It is possible to narrow the element pitch since it is possible to reduce the size of the elements compared to the bulk ultrasonic elements due to the ultrasonic elements being configured as described above. Due to this, it is possible to suppress the generation of grating lobes. In addition, it is possible to configure a driving circuit using a circuit element with low resistance to voltage since driving is possible using voltage amplitude which is small compared to bulk ultrasonic elements.

2. COMPARATIVE EXAMPLE

Figure 2:
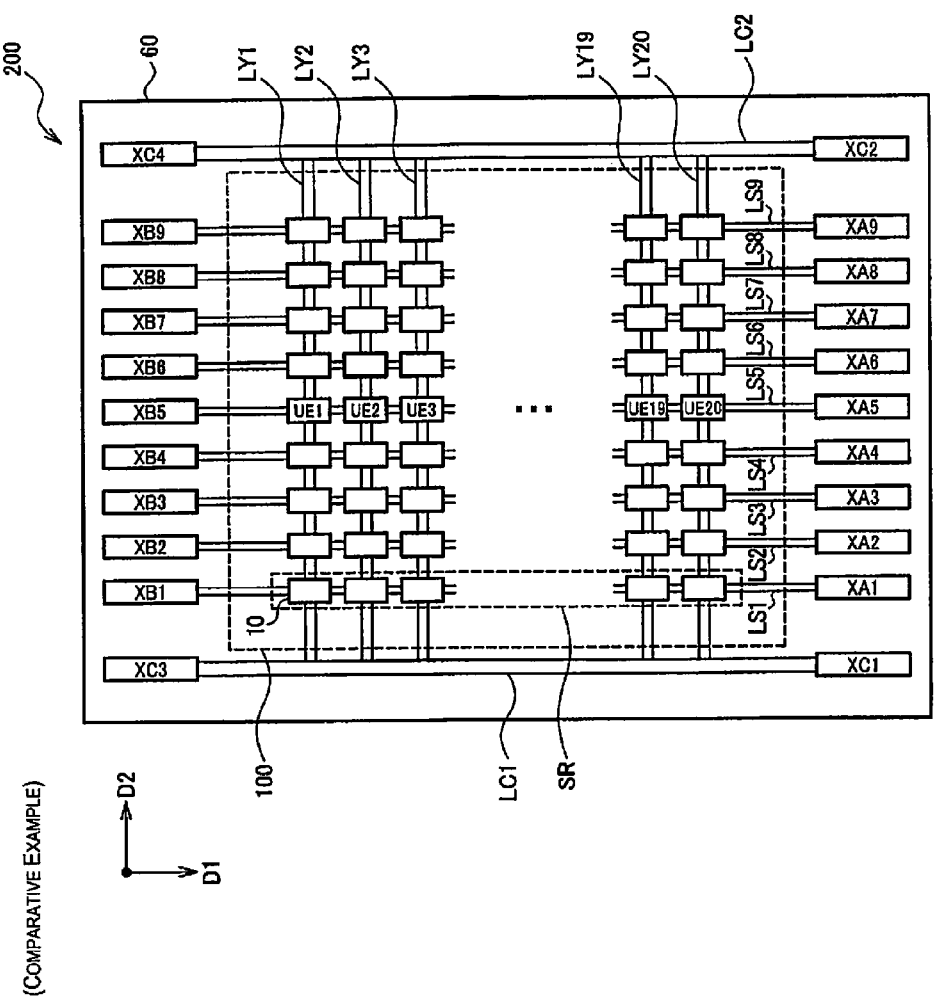
FIG. 2 is a comparative example of an ultrasonic transducer device.

FIG. 2 illustrates a comparative example of the ultrasonic transducer device of the present embodiment. A first direction D1 shown in FIG. 2 corresponds to a slice direction in a scanning operation of an ultrasonic beam and a second direction D2 which intersects with (for example, is orthogonal to) the first direction corresponds to a scanning direction in a scanning operation of an ultrasonic beam.

An ultrasonic transducer device 200 of the comparative example includes the substrate 60, an ultrasonic element array 100 which is arranged on the substrate 60, signal electrode wirings LS1 to LS9 which are arranged on the substrate 60 along the first direction D1, signal terminals XA1 to XA9 which are connected to ends of the signal electrode wirings LS1 to LS9, signal terminals XB1 to XB9 which are connected to the other ends of the signal electrode wirings LS1 to LS9, common electrode wirings LC1 and LC2 which are arranged on the substrate 60 along the first direction D1, common terminals XC1 and XC2 which are connected to ends of the common electrode wirings LC1 and LC2, common terminals XC3 and XC4 which are connected to the other ends of the common electrode wirings LC1 and LC2, and common electrode wirings LY1 to LY20 where one end is connected to the common electrode wiring LC1 and the other end is connected to the common electrode wiring LC2.

The ultrasonic element array 100 has nine rows of ultrasonic element rows SR which are arranged along the second direction D2 and the ultrasonic element rows SR have twenty of the ultrasonic elements 10 which are arranged along the first direction D1. That is, the ultrasonic elements 10 are arranged in the ultrasonic element array 100 in a matrix formation with 20 lines by 9 rows. One of the electrodes (for example, the lower electrodes) in each of the $1^{st}$ to the $9^{th}$ rows of the ultrasonic elements 10 are respectively connected to the signal electrode wirings LS1 to LS9 and the other of the electrodes (for example, the upper electrodes) in each of the $1^{st}$ to the $20^{th}$ lines of the ultrasonic elements 10 are respectively connected to the common electrode wirings LY1 to LY20.

Figure 3:
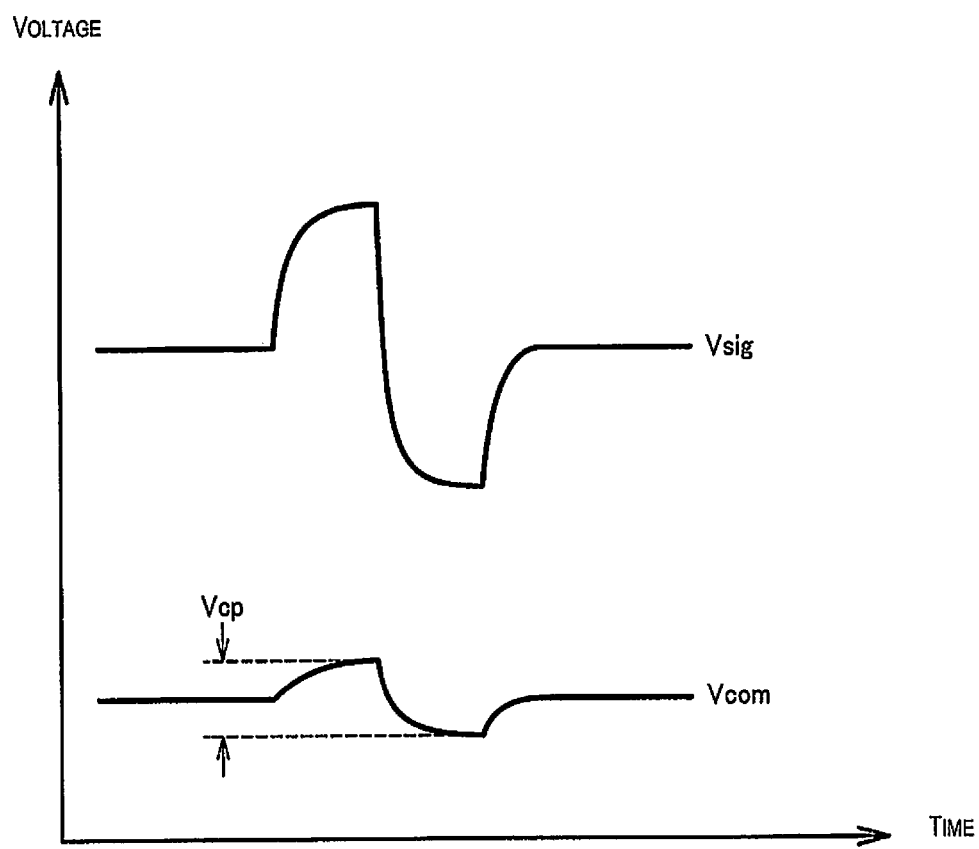
FIG. 3 is a waveform example of a voltage of a signal electrode of an ultrasonic element and a voltage of a common electrode of an ultrasonic element.

FIG. 3 symmetrically illustrates an example of waveforms of a voltage Vsig from a signal electrode of the ultrasonic element 10 and a voltage Vcom from a common electrode of the ultrasonic element 10. Since a capacity component can be seen between the electrodes of the ultrasonic element 10, an electric current flows in the common electrode wiring via the common electrode when the voltage Vsig from the signal electrode varies and the voltage Vcom from the common electrode varies due to wiring impedance in the common electrode wiring. Voltage amplitude of this variance is set as Vcp.

In the comparative example described above, the wiring impedance in the common electrode wiring increases from common terminals XC1 to XC4 to the ultrasonic elements 10 approaching the center of the ultrasonic element array 100 since the common terminals XC1 to XC4 are arranged in the four corners of the ultrasonic element array 100. As a result, the voltage amplitude Vcp of the common electrode increases approaching the center of the ultrasonic element array 100, and the actual voltage amplitude of the voltage (Vsig-Vcom) which is applied between the electrodes in the ultrasonic element 10 is reduced.

Figure 4:
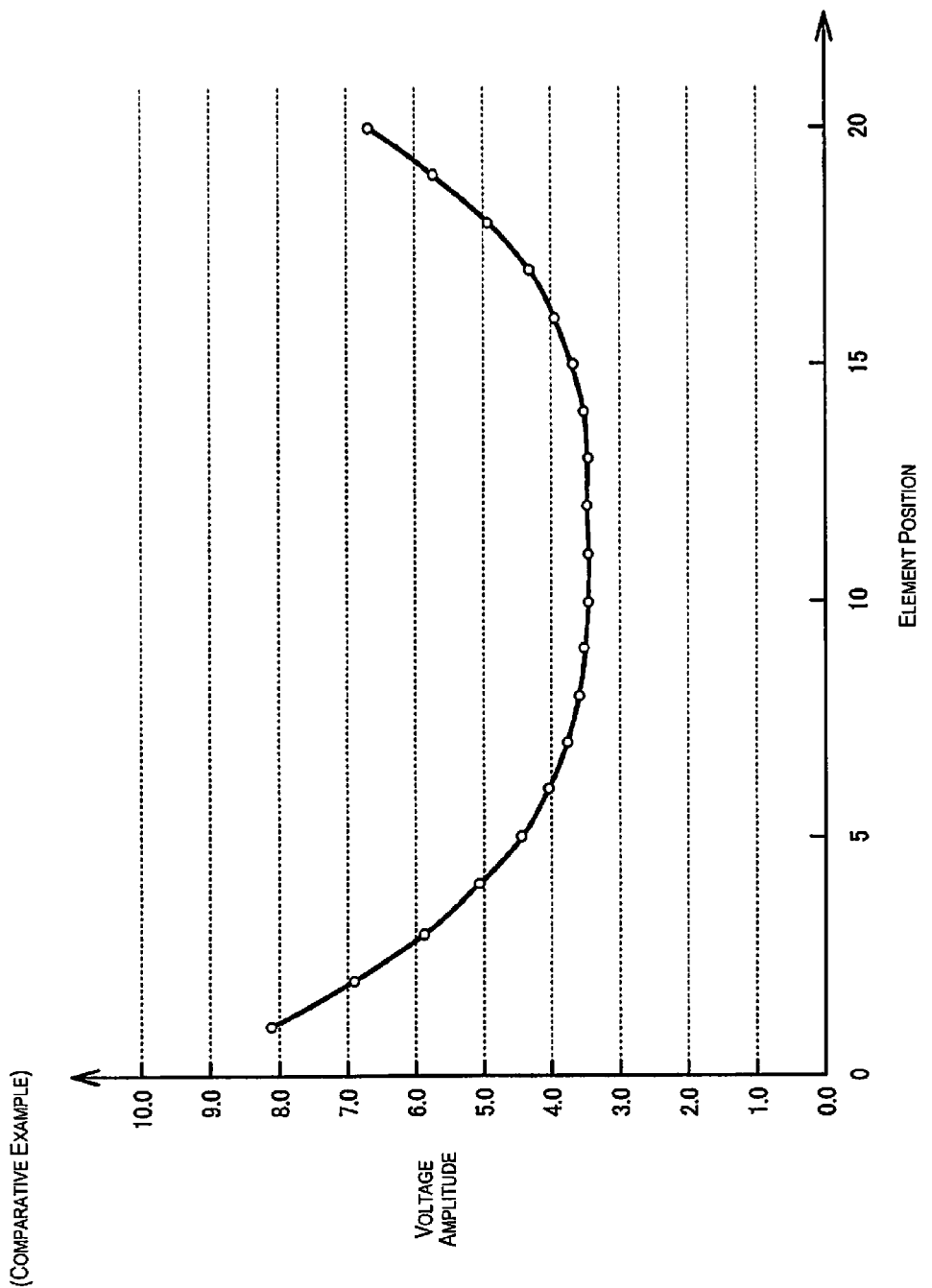
FIG. 4 is a characteristic example of voltage amplitude which is applied between electrodes of an ultrasonic element in a comparative example.

FIG. 4 illustrates a characteristic example of voltage amplitude which is applied between the electrodes in the ultrasonic element 10. The characteristic example is the results of a simulation in a case of the comparative example in FIG. 2 where a driving signal which is shared is supplied to the signal terminals XA5 and XB5 which are central, a fixed voltage is supplied to the signal terminals XA1 to XA4, XA6 to XA9, XB1 to XB4, and XB6 to XB9 which are on both sides, and a common voltage which is shared is supplied to the common terminals XC1 to XC4. The frequency of the driving signal was 3.5 MHz. Element positions 1 to 20 on the horizontal axis are numbers for the lines of the ultrasonic elements and correspond to ultrasonic elements UE1 to UE20 which are connected to the signal terminals XA5 and XB5.

As shown in FIG. 4, the voltage amplitude between the electrodes increases closer to the ends of the ultrasonic element array 100 and the voltage amplitude between the electrodes is smaller closer to the center. When there are deviations and a reduction in the voltage amplitude in this manner, there is a problem in that a reduction in the sound field, deviations in the sound field, or breaks in the sound field of an ultrasonic beam or the like may be generated.

3. Ultrasonic Transducer Device

3.1. FIRST CONFIGURATION EXAMPLE

Figure 5:
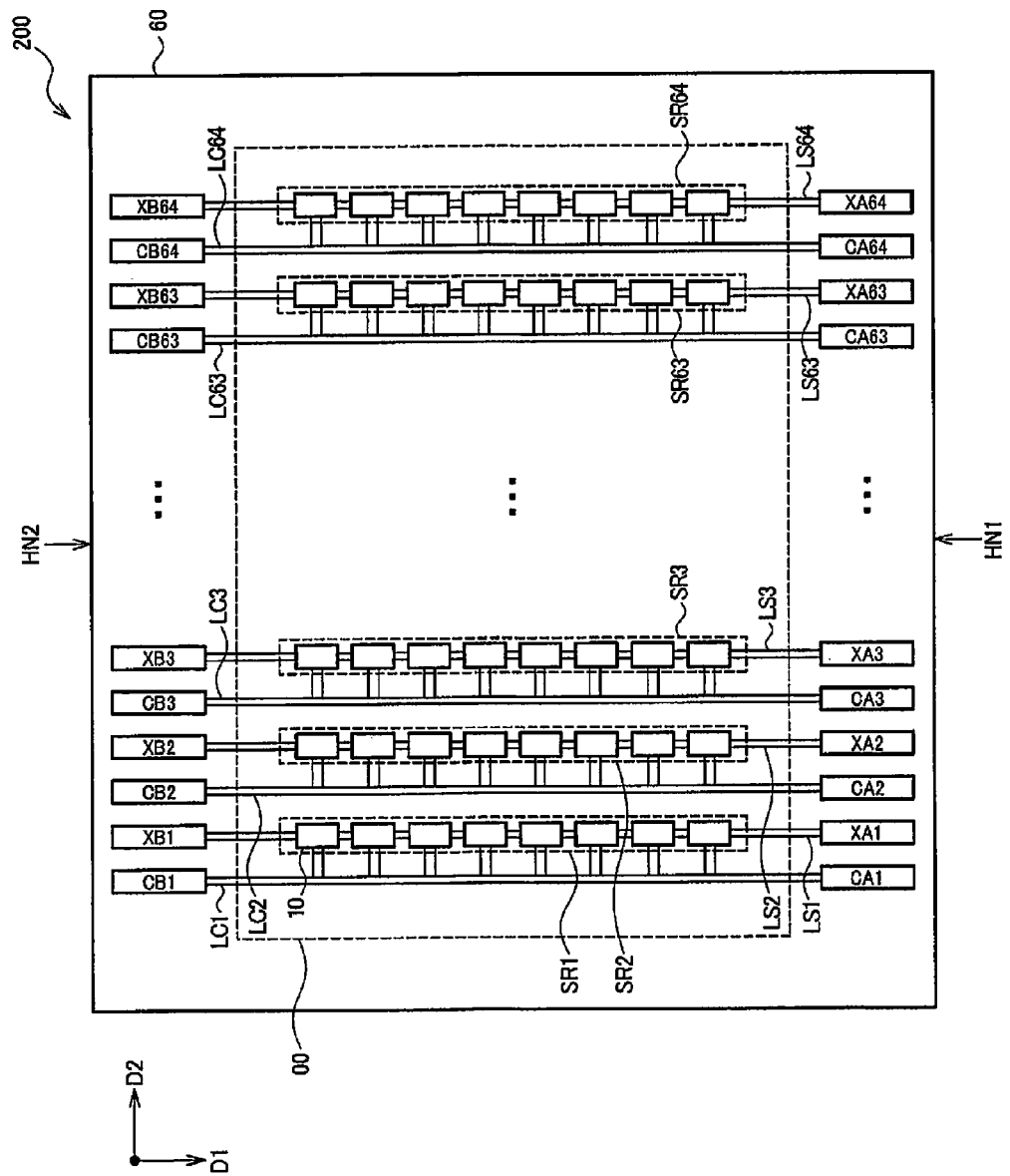
FIG. 5 is a first configuration example of an ultrasonic transducer device.

FIG. 5 illustrates a first configuration example of the ultrasonic transducer device 200 of the present embodiment which is able to solve the problems described above. Below, an example will be described in a case where the ultrasonic element array 100 is an array with a matrix formation of 8 lines by 64 rows, but the present embodiment is not limited to this, and the values of m and n of m lines by n rows may be values other than m=8 and n=64.

Here, it is possible to adopt a transducer which is a type which uses a piezoelectric element as described above (a thin film piezoelectric element) as the ultrasonic transducer device 200, but the present embodiment is not limited to this. For example, a transducer which is a type which uses a capacitive element such as a c-MUT (Capacitive Micro-machined Ultrasonic Transducer) may be adopted.

The ultrasonic transducer device 200 includes the substrate 60, the ultrasonic element array 100 which is formed on the substrate 60, $1^{st}$ to $64^{th}$ one end side signal terminals XA1 to XA64 (first end signal terminals) which are formed on the substrate 60, $1^{st}$ to $64^{th}$ other end side signal terminals XB1 to XB64 (second end signal terminals) which are formed on the substrate 60, $1^{st}$ to $64^{th}$ one end side common terminals CA1 to CA64 (first end common terminals) which are formed on the substrate 60, $1^{st}$ to $64^{th}$ other end side common terminals CB1 to CB64 (second end common terminals) which are formed on the substrate 60, $1^{st}$ to $64^{th}$ signal electrode wirings LS1 to LS64 which are formed on the substrate 60, and $1^{st}$ to $64^{th}$ common electrode wirings LC1 to LC64 which are formed on the substrate 60.

The ultrasonic element array 100 includes $1^{st}$ to $64^{th}$ ultrasonic element rows SR1 to SR64 which are arranged along the second direction D2 (the scanning direction) and each of the ultrasonic element rows in the ultrasonic element rows SR1 to SR64 includes eight of the ultrasonic elements 10 which are arranged along the first direction D1 (the slice direction).

One end side common terminals CA1 to CA64 are arranged at one end portion of the ultrasonic element array 100 in the first direction D1. The other end side common terminals CB1 to CB64 are arranged at the other end portion of the ultrasonic element array 100 in the first direction D1. The one end side signal terminals XA1 to XA64 are arranged at one end portion of the ultrasonic element array 100 in the first direction D1. The other end side signal terminals XB1 to XB64 are arranged at the other end portion of the ultrasonic element array 100 in the first direction D1.

For example, the substrate 60 has a rectangular shape with the second direction D2 as the long-side direction, and the one end side common terminals CA1 to CA64 and the one end side signal terminals XA1 to XA64 are alternately arranged along a first long side HN1 of the rectangular shape. In addition, the other end side common terminals CB1 to CB64 and the other end side signal terminals XB1 to XB64 are alternately arranged along a second long side HN2 of the rectangular shape.

The common electrode wirings LC1 to LC64 are arranged along the first direction D1 and are respectively connected to the ultrasonic element rows SR1 to SR64. One end of the common electrode wirings LC1 to LC64 is connected to the one end side common terminals CA1 to CA64 and the other end of the common electrode wirings LC1 to LC64 is connected to the other end side common terminals CB1 to CB64.

If the ultrasonic element row SR1 is taken as an example, a common voltage which is the same voltage is supplied to the common terminals CA1 and CB1, and the common voltage is supplied to the common electrodes (for example, the upper electrodes) of the ultrasonic elements 10 which configure the ultrasonic element row SR1 via the common electrode wiring LC1. The common voltage is supplied via each of the common electrode wirings LC2 to LC64 in the same manner with respect to the ultrasonic element rows SR2 to SR64.

In this manner, the length of wiring from the common terminal to the ultrasonic element is short compared to the comparative example described above since the common electrode wirings are provided with respect to each of the ultrasonic element rows, and in addition, the number of ultrasonic elements which are connected to the one line of the common electrode terminals is smaller. Due to this, it is possible for the voltage amplitude which is applied between the terminals in the ultrasonic element to approach the end and central sections of the ultrasonic element array 100 and it is possible to suppress a reduction in the sound field in the center section.

Here, the common voltage which is the same voltage may be supplied to the common terminals CA1 to CA64 (and to the corresponding common terminals CB1 to CB64) or common voltages which are different voltages may be supplied. For example, in a case where there are the ultrasonic element rows dedicated to transmission and the ultrasonic element rows dedicated to reception, the common voltage with respect to the ultrasonic element rows dedicated to transmission and the common voltage with respect to the ultrasonic element rows dedicated to reception may be voltages which are different.

The signal electrode wirings LS1 to LS64 are arranged along the first direction D1 and are respectively connected to the ultrasonic element rows SR1 to SR64. One end of the signal electrode wirings LS1 to LS64 is connected to the one end side signal terminals XA1 to XA64 and the other end of the signal electrode wirings LS1 to LS64 is connected to the other end side signal terminals XB1 to XB64.

If the ultrasonic element row SR1 is taken as an example, a driving signal which has the same waveform and is the same voltage is supplied to the signal terminals XA1 and XB1 and the driving signal is supplied to the signal electrodes (for example, the lower electrodes) of the ultrasonic elements 10 which configure the ultrasonic element row SR1 via the signal electrode wiring LS1. The driving signal is supplied via each of the signal electrode wirings LS2 to LS64 in the same manner with respect to the ultrasonic element rows SR2 to SR64.

Here, since there is wiring impedance in the signal electrode wiring and a capacity component of the ultrasonic elements, the driving signal which is applied to the signal terminals attenuates in accordance with being transmitted on the signal electrode wiring. In this point, since the driving signal is supplied from both ends of the signal electrode wiring in the present embodiment, it is possible to suppress attenuation of the driving signal compared to a case where the driving signal is only applied from one end. In addition, deviation in the sound field is generated in the slice direction (the first direction D1) due to attenuation of the driving signal in a case where the driving signal is only applied from one end, but it is possible to suppress deviation in the sound field since the attenuation of the driving signal is symmetrical in the present embodiment.

Here, as described above, an example is described where the ultrasonic element array 100 is an arrangement with a matrix formation of m lines by n rows, but the present embodiment is not limited to this and the ultrasonic element array 100 may be an arrangement with an array formation where a plurality of unit elements (the ultrasonic elements) are arranged to have regularity in two dimensions. For example, the ultrasonic element array 100 may be a zigzag arrangement. Here, the arrangement with a matrix formation is an arrangement with a grid formation of m lines by n rows and includes not only cases where the grid is a rectangular shape but cases where the grid is changed to a parallelogram. The arrangement with a zigzag shape is an arrangement where m rows of the ultrasonic elements and m−1 rows of the ultrasonic elements are alternately lined up, the m rows of the ultrasonic elements are arranged in odd lines out of (2m−1) lines, and the m−1 rows of the ultrasonic elements are arranged in even lines out of (2m−1) lines.

Figure 6:
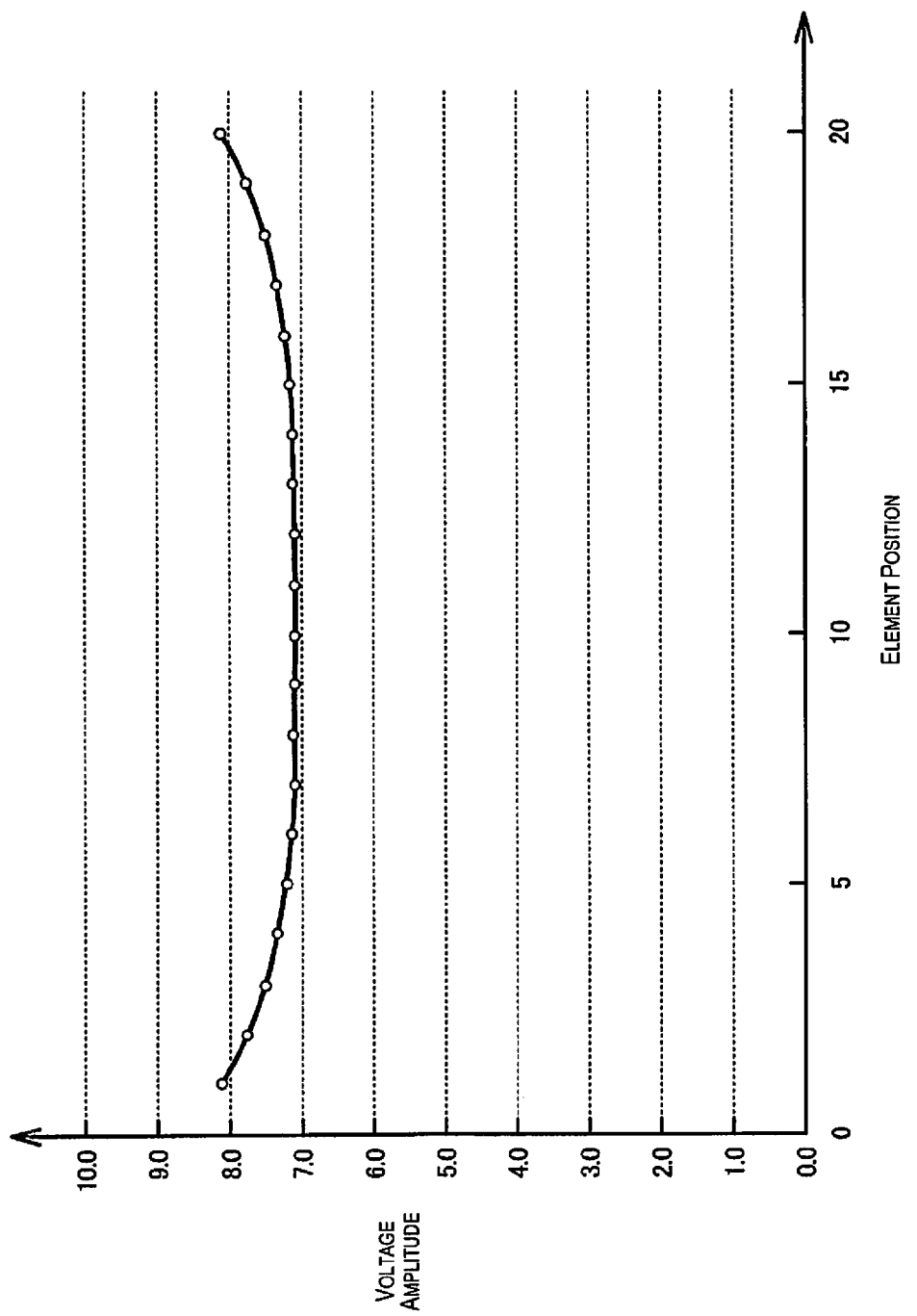
FIG. 6 is a characteristic example of voltage amplitude which is applied between electrodes of an ultrasonic element in an embodiment.

FIG. 6 illustrates a characteristic example of voltage amplitude which is applied between the electrodes in the ultrasonic element 10. The characteristic example is the results of a simulation in a case of the first configuration example described above where the ultrasonic element rows are configured into 20 lines by 9 rows (m=20 and n=9), a driving signal which is shared is supplied to the signal terminals XA5 and XB5 which are in the center of the nine rows, a fixed voltage is supplied to the signal terminals XA1 to XA4, XA6 to XA9, XB1 to XB4, and XB6 to XB9 which are on both sides, and a common voltage which is the same voltage is supplied to the common terminals XC1 to XC9. The frequency of the driving signal was 3.5 MHz. The element positions 1 to 20 on the horizontal axis are numbered for the lines of the ultrasonic elements.

As shown in FIG. 6, there is a difference of approximately 1 V in the voltage amplitude between the electrodes at the end and the center sections of the ultrasonic element array 100, but the reduction in the voltage amplitude is substantially suppressed at the center section compared to the comparative example in FIG. 4. In this manner, it is possible to realize an improvement in sound pressure, suppression of deviations in the sound field, suppression of breaks in the sound field of an ultrasonic beam and the like since deviations and a reduction in the voltage amplitude are suppressed in the present invention.

FIG. 7A and FIG. 7B illustrate a characteristic example of distribution of radiated sound pressure. FIG. 7A illustrates a characteristic example with the same conditions as the comparative example in FIG. 4 and FIG. 7B illustrates a characteristic example with the same conditions as the present embodiment in FIG. 6. The horizontal axis represents a position in a direction along an element row where a driving signal is applied and x=0 mm corresponds to the center of the element row. Depth represents distance in a direction which is orthogonal to the plane of the substrate 60 from the substrate 60 to a measurement point.

In the comparative example, the highest sound pressure at a depth of 50 mm is 2925 Pa and the highest sound pressure at a depth of 100 mm is 1557 Pa. On the other hand, in the present embodiment, the highest sound pressure at a depth of 50 mm is 4825 Pa and the highest sound pressure at a depth of 100 mm is 2497 Pa. It is understood that there is a substantial improvement in the highest sound pressure in the present embodiment at any depth.

3.2 SECOND CONFIGURATION EXAMPLE

In the first configuration example described above, a case is described where one row of the ultrasonic element rows is connected to one channel which receives and transmits the same signal, but the present embodiment is not limited to this and a plurality of rows of the ultrasonic element rows may be connected to one channel.

Figure 8:
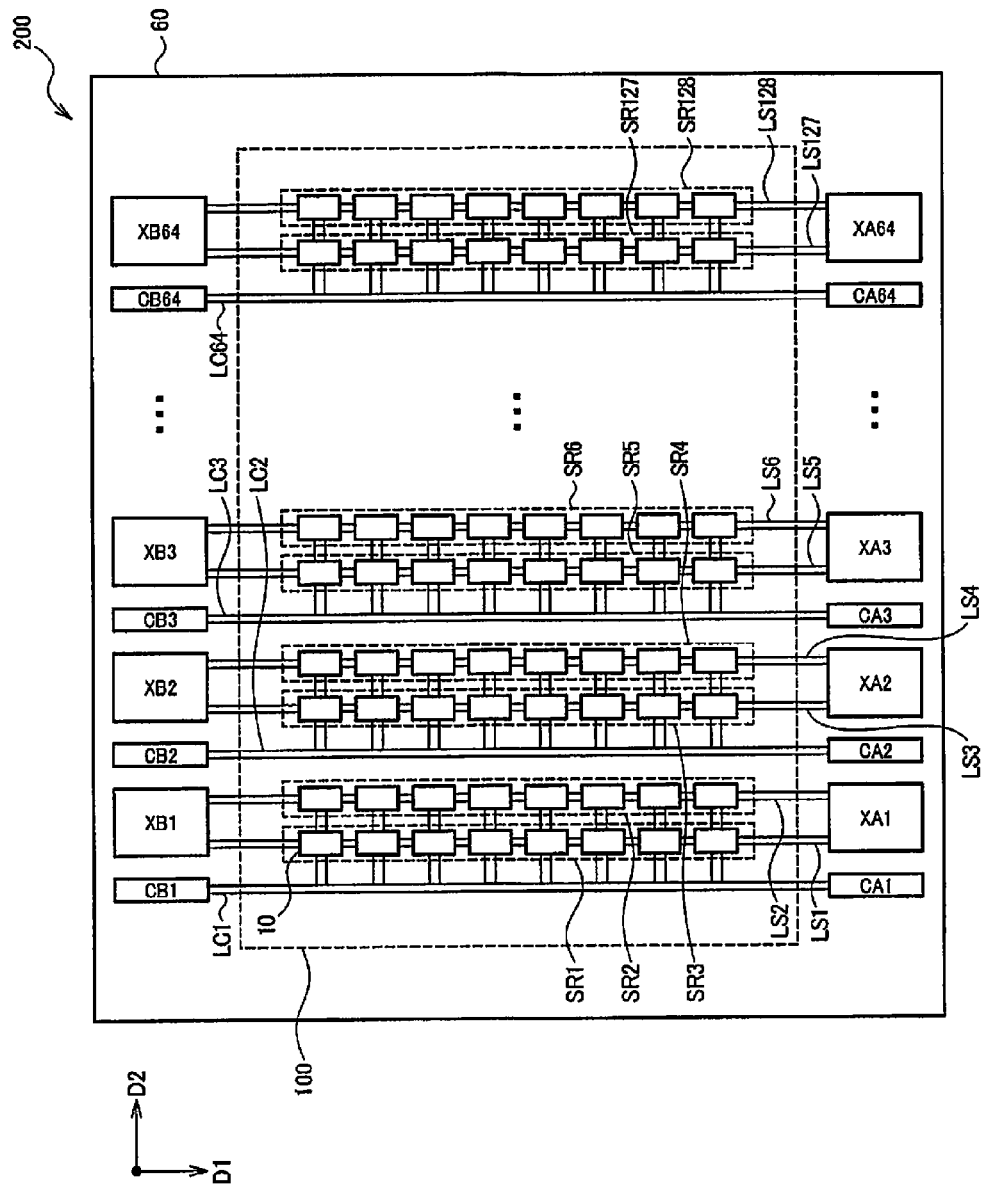
FIG. 8 is a second configuration example of an ultrasonic transducer device.

FIG. 8 illustrates a second configuration example of the ultrasonic transducer device as a configuration example in the case described above. An example will be described below in a case where two rows of the ultrasonic element rows are connected to one channel, but three or more rows of the ultrasonic element rows may be connected to one channel. In addition, a different number of rows of the ultrasonic element rows may be connected to the respective channels.

The ultrasonic transducer device 200 includes the substrate 60, the ultrasonic element array 100, the $1^{st}$ to $64^{th}$ one end side signal terminals XA1 to XA64, the $1^{st}$ to $64^{th}$ other end side signal terminals XB1 to XB64, the $1^{st}$ to $64^{th}$ one end side common terminals CA1 to CA64, the $1^{st}$ to $64^{th}$ other end side common terminals CB1 to CB64, $1^{st}$ to $128^{th}$ signal electrode wirings LS1 to LS128, and the $1^{st}$ to $64^{th}$ common electrode wirings LC1 to LC64. Here, the constituent elements which are the same as the constituent elements described in FIG. 5 are given the same reference numerals and description is appropriately omitted.

The ultrasonic element array 100 includes $1^{st}$ to $128^{th}$ ultrasonic element rows SR1 to SR128 which are arranged along the second direction D2 (the scanning direction).

The common electrode wirings LC1 to LC64 are each connected with two rows of the ultrasonic element rows. For example, the common electrode wiring LC1 is connected with the common electrodes (for example, the upper electrodes) in the ultrasonic elements 10 which configure the ultrasonic element rows SR1 and SR2.

The signal electrode wirings LS1 to LS128 are respectively connected with the ultrasonic element rows SR1 to SR128. The one end side signal terminals CA1 to XA64 are each connected with one end of the two lines of the signal electrode wirings, and the other end side signal terminals XB1 to XB64 are each connected with the other end of the two lines of the signal electrode wirings. For example, the signal electrode wiring LS1 is connected with the signal electrodes (for example, the lower electrodes) in the ultrasonic elements 10 which configure the ultrasonic element row SR1, and the signal electrode wiring LS2 is connected with the signal electrodes (for example, the lower electrodes) in the ultrasonic elements 10 which configure the ultrasonic element row SR2. One out of the ends of the signal electrode wirings LS1 and LS2 are connected with the signal terminal XCA1 and the other ends of the signal electrode wirings LS1 and LS2 are connected with the signal terminal XB1.

In this manner, it is possible to increase the number of the ultrasonic elements which are connected to one channel by connecting a plurality of rows of the ultrasonic element rows to one channel. Due to this, it is possible to improve the sound pressure of the transmission ultrasonic waves.

Here, a case is described where one line of the common electrode wirings is connected with one channel which receives and transmits the same signal, but the present invention is not limited to this, and for example, one line of the common electrode wirings may be connected with a plurality of channels or a plurality of lines of the common electrode wirings may be connected to one channel.

In the embodiment described above, for example, the ultrasonic transducer device 200 includes the ultrasonic element array 100 and the common electrode wirings (for example LC2) as shown in FIG. 5. The ultrasonic element array 100 has three rows (for example, SR1 to SR3) of the ultrasonic element rows where a plurality of the ultrasonic elements 10 which are electrically connected are arranged in the first direction D1. The common electrode wiring (LC2) supplies a common voltage to one row of the ultrasonic element rows (SR2) out of the three rows of the ultrasonic element rows (SR1 to SR3). The three rows of the ultrasonic element rows (SR1 to SR3) are arranged in the second direction D2 which intersects with (for example, is orthogonal to) the first direction D1. The common electrode wiring (LC2) is arranged in the first direction D1 and is arranged between two rows of the ultrasonic element rows (SR1 and SR3) which are positioned on the outer sides out of the three rows of the ultrasonic element rows (SR1 to SR3).

According to this, the common electrode wiring (LC2) is arranged between the three rows of the ultrasonic element rows (SR1 to SR3) and it is possible to supply a common voltage to at least one row of the ultrasonic element rows (SR2) out of the three rows of the ultrasonic element rows (SR1 to SR3) using the common electrode wirings (LC2). Due to this, the length of common electrode wiring from the common terminal to the ultrasonic element is short and wiring impedance is reduced compared to a case where the common electrode wirings are arranged at both ends of the ultrasonic element array 100 as described in FIG. 6 and the like. As a result, it is possible to suppress a reduction in the actual voltage amplitude even at the center section of the ultrasonic element array 100, and it is possible to suppress a reduction in sound pressure and the like as described in FIG. 7B and the like.

Here, "arranged in the first direction D1 (or the second direction D2)" specifically refers to an arrangement along the first direction D1 (or the second direction D2). For example, in a case where a plurality of the ultrasonic elements 10 are arranged along the first direction D1, this is not limited to a cases where the plurality of the ultrasonic elements 10 are lined up on a straight line along the first direction D1 and the plurality of the ultrasonic elements 10 may be arranged in a zigzag with respect to a straight line along the first direction D1.

Here, the three rows of the ultrasonic element rows are three arbitrary rows out of a plurality of the ultrasonic element rows which are included in the ultrasonic element array 100. For example, the three rows are the ultrasonic element rows SR1 to SR3. In this case, the two rows on the outer sides are the ultrasonic element rows SR1 and SR3 and the common electrode wiring between the ultrasonic element rows SR1 and SR3 is the common electrode wiring LC2. Alternatively, the three rows are the ultrasonic element rows SR1, SR3 and SR5. In this case, the two rows on the outer sides are the ultrasonic element rows SR1 and SR5 and the common electrode wiring between the ultrasonic element rows SR1 and SR5 is the common electrode wiring LC2 or the common electrode wiring LC3. Alternatively, the three rows may be the ultrasonic element row SR1, any of the ultrasonic element rows SR2 to SR63, and the ultrasonic element row SR64. In this case, the two rows on the outer sides are the ultrasonic element rows SR1 and SR64 and the common electrode wiring between the ultrasonic element rows SR1 and SR64 is any of the common electrode wirings LC2 to LC64.

In addition, in the present embodiment, the ultrasonic element array 100 has a $1^{st}$ to an $n^{th}$ of the ultrasonic element rows (for example, SR1 to SR64) which are arranged along the second direction D2 and include the three rows of the ultrasonic element rows (SR1 to SR3). The common electrode wiring (LC2) supplies the common voltage to an to a $j^{th}$ of the ultrasonic element rows (for example, SR2) out of the $1^{st}$ to the $n^{th}$ of the ultrasonic element rows and is arranged between a $k^{th}$ of the ultrasonic element rows (SR1) and a $k+1^{th}$ of the ultrasonic element rows (SR2) out of the $i-1^{th}$ to the $j^{th}$ of the ultrasonic element rows (SR1 and SR2).

Here, i and j are natural numbers such that $i \leq j \leq n-1$ and k is a natural number such that $i-1 \leq k \leq j$. For example, in a case where the common electrode wiring (LC2) supplies the common voltage to the second of the ultrasonic element rows (SR2 where $i=j=2$) as in FIG. 5, the common electrode wiring (LC2) may be arranged between the first and the second of the ultrasonic element rows (SR1 and SR2 where $k=1=i-1$). Alternatively, the arrangement in FIG. 5 may be reversed in terms of left and right and the common electrode wiring (LC2) may be arranged between the second and the third of the ultrasonic element rows (SR2 and SR3 where $k=2=j$).

According to this, it is possible to arrange the common electrode wiring (LC2), which supplies the common voltage to the $i^{th}$ to the $i^{th}$ of the ultrasonic element rows (SR2), between the $k^{th}$ of the ultrasonic element rows (for example, SR1) and the $k+1^{th}$ of the ultrasonic element rows (SR2). Due to this, it is possible to supply the common voltage with a low resistance with respect to the $i^{th}$ to the $i^{th}$ of the ultrasonic element rows (SR2) and it is possible to suppress a reduction in voltage amplitude which is applied to the ultrasonic elements.

In addition, in the present embodiment, the substrate 60 where the ultrasonic element array 100 is arranged and the common electrode wiring (LC2) is formed and the signal electrode wiring (LS2) which is formed on the substrate 60 and performs at least one of supplying and receiving of signals with respect to the ultrasonic element rows (for example, SR2) are included. Each of the ultrasonic elements in the plurality of ultrasonic elements 10 has the first electrode (for example, the portion where the first electrode layer 21 covers the piezoelectric body layer 30), the second electrode (for example, the second electrode layer 22 at the portion which is covered by the piezoelectric body layer 30), and the transducer section (for example, the piezoelectric body layer 30) which is provided between the first electrode and the second electrode. The first electrode may be connected to the signal electrode wiring (for example, LS2), and the second electrode may be connected to the common electrode wiring (LC2).

For example, in the present embodiment, the common electrode wirings and the signal electrode wirings are formed to extend on the substrate 60. Formed to extend refers to a conductive layer (a wiring layer) being laminated on the substrate 60 using, for example, an MEMS process, a semiconductor process, or the like and at least two points (for example, from the ultrasonic element to the signal terminal) being connected using the conductive layer.

In a case where the common electrode wiring (LC2) is formed on the substrate 60, there is a possibility that wiring resistance will be generated in the common electrode wiring (LC2), but according to the present embodiment, it is possible to connect from the common terminal (CA2) to the ultrasonic element 10 with low resistance even in a case such as this and it is possible to suppress a reduction in voltage amplitude which is applied to the ultrasonic element 10.

In addition, in the present embodiment, the ultrasonic transducer device 200 includes the plurality of signal electrode wirings LS1 to LS64, the first common electrode wiring (LC2) as the common electrode wiring (LC2) described above, and the second and third common electrode wirings (for example, LC3 and LC4). Each of the signal electrode wirings of the plurality of signal electrode wirings LS1 to LS64 is arranged in the first direction D1. In addition, each of the signal electrode wirings performs at least one of supplying and receiving of signals with respect to any of the plurality of the ultrasonic element rows SR1 to SR64 which are at least the first and the second of the ultrasonic element rows. Each of the common electrode wirings of the first to the third common electrode wirings (LC2 to LC4) is arranged in the first direction D1 and supplies the common voltage with respect to one or a plurality of the ultrasonic element rows out of the plurality of the ultrasonic element rows SR1 to SR64.

According to this, at least the first common electrode wiring (for example, LC2 in FIG. 5) is arranged between the ultrasonic element rows and it is possible to supply the common voltage to each of one or a plurality of the ultrasonic element rows (for example, each of SR2 to SR4 in FIG. 5) using the first to the third common electrode wirings (LC2 to LC4). Due to this, it is possible to suppress a reduction in voltage amplitude which is applied to the ultrasonic elements since it is possible for wiring resistance from the common electrode to the ultrasonic terminal to be smaller.

In addition, in the present embodiment, the first common electrode wiring (for example, LC2 in FIG. 5) is electrically connected to the $1^{st}$ to a $p^{th}$ (where p is a natural number) of the ultrasonic element rows (SR2) and is electrically not connected to the $p+1^{th}$ to a $q^{th}$ (where q is a natural number such that q>p) of the ultrasonic element rows (SR3). The second common electrode wiring (LC3) is electrically connected to the $p+1^{th}$ to the $q^{th}$ of the ultrasonic element rows (SR3) and is electrically not connected to the $1^{st}$ to the $p^{th}$ of the ultrasonic element rows (SR2).

According to this, it is possible to suppress crosstalk between the ultrasonic element rows via variation in voltage in the common electrode since it is possible to separate the common electrode wiring (LC2) which is connected to the $1^{st}$ to the $p^{th}$ of the ultrasonic element rows (SR2) and the common electrode wiring (LC3) which is connected to the $p+1^{th}$ to the $q^{th}$ of the ultrasonic element rows (SR3). For example, the $1^{st}$ to the $p^{th}$ of the ultrasonic element rows (SR2) for a continuous wave Doppler effect are set for receiving and the $p+1^{th}$ to the $q^{th}$ of the ultrasonic element rows (SR3) are set for transmitting. Assuming that the common electrode wirings are shared, the common voltage would vary due to the driving signal, this variation would have an effect on the ultrasonic element rows for receiving, and it would not be possible to detect a weak reception signal. In this point, it is possible to detect a weak reception signal according to the present embodiment since the common voltage for the ultrasonic element rows for receiving is independent.

In addition, in the present embodiment, the ultrasonic transducer device 200 includes the first and second common terminals (CA2 and CA3) which are connected to the first and second common electrode wirings (for example, LC2 and LC3 in FIG. 8), the first signal terminal (XA2) which is connected together (in common) with the $1^{st}$ to an $r^{th}$ (where r is a natural number) of the signal electrode wirings (LS3 and LS4), and the second signal terminal (XA3) which is connected together (in common) with a $k+1^{th}$ to a $2k^{th}$ of the signal electrode wirings (LS5 and LS6). The first common electrode wiring (LC2) and the $1^{st}$ to the $k^{th}$ of the signal electrode wirings (LS3 and LS4) are electrically connected to the $1^{st}$ to the $k^{th}$ of the ultrasonic element rows (SR3 and SR4). The second common electrode wiring (LC3) and the $k+1^{th}$ to the $2k^{th}$ of the signal electrode wirings (LS5 and LS6) are electrically connected to the $k+1^{th}$ to the $2k^{th}$ of the ultrasonic element rows (SR5 and SR6).

According to this, it is possible to suppress crosstalk between channels via variation in voltage in the common electrode wirings since it is possible to separate the common electrode wirings for each channel which performs at least transmitting and receiving of the same signal. For example, it is possible to allocate channels for reception and channels for transmission in a case where a continuous wave Doppler effect described above is used.

In addition, in the present embodiment, the common electrode wiring (for example, LC1 or the like) is formed on the substrate 60 so that a difference between the potential of the common electrode in the first ultrasonic element 10, which is arranged at a corner of the ultrasonic element array 100, and the potential of the common electrode of the second ultrasonic element 10, which is arranged at the center of the ultrasonic element array 100, is not generated.

Here, "so that a difference in potential is not generated" refers to, for example, the difference in potential being within a specific range. The specific range is a difference in potential between the common electrodes at the corner and the center of the ultrasonic element array 100 where it is possible for a desired ultrasonic beam shape to be realized. For example, the voltage amplitude which is to be applied between the electrodes in the ultrasonic elements is determined so as to realize the desired ultrasonic beam shape and a permissible error in the common voltage is determined so as to realize this voltage amplitude. Then, the common electrode wiring (for example, LC1 or the like) is formed so that the permissible error is in the range.

According to this, it is possible to not generate a difference between the potential of the common voltage which is supplied to an end section of the ultrasonic element array 100 and the common voltage which is supplied to the central section of the ultrasonic element array 100. Due to this, it is possible to suppress a reduction in driving voltage amplitude at the central section of the ultrasonic element array 100 since variation in the common voltage due to wiring resistance as described in FIG. 3 is small.

4. Detailed Configuration of Ultrasonic Transducer Device

Figure 9B:
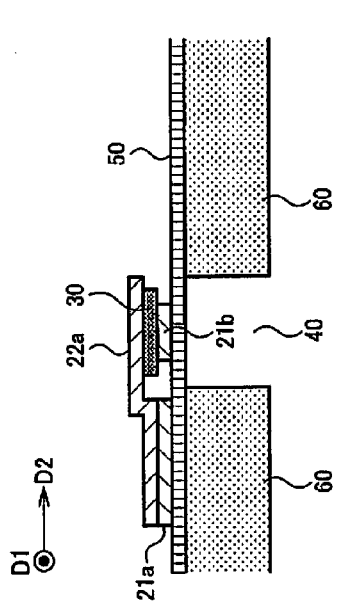
FIGS. 9A to 9C are first detailed configuration examples of an ultrasonic transducer device.
Figure 9C:
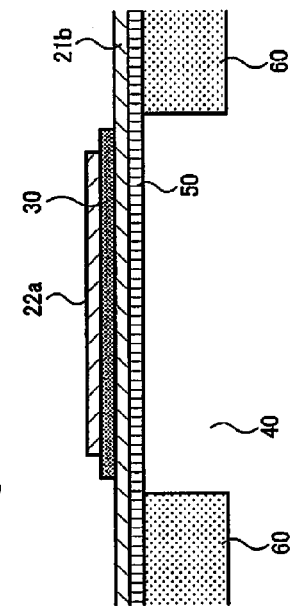
Figure 9A:
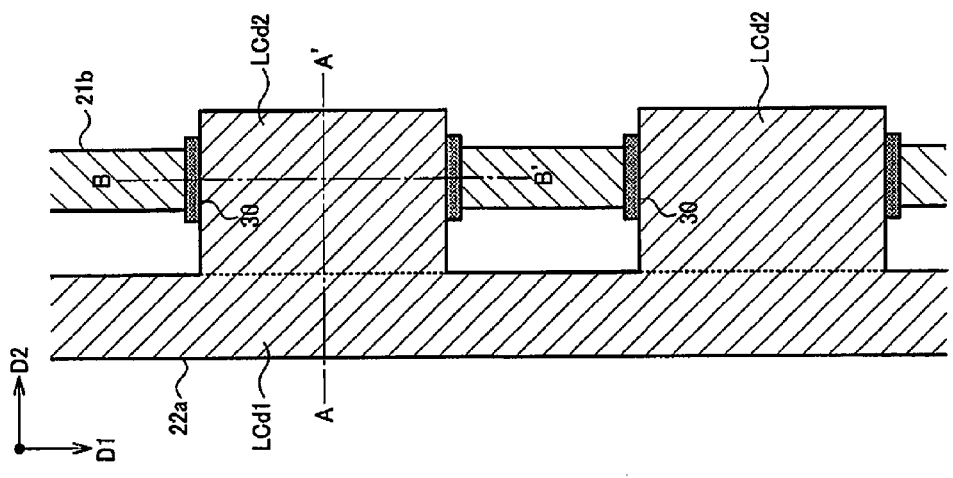

FIGS. 9A to 9C illustrate a first detailed configuration example of the ultrasonic transducer device 200. FIG. 9A is a plan view diagram with a plan view of the substrate 60, FIG. 9B is a cross sectional diagram at an AA' cross section of FIG. 9A, and FIG. 9C is a cross sectional diagram at a BB' cross section of FIG. 9A.

The ultrasonic transducer device 200 includes the substrate 60, the vibrating film 50, the piezoelectric body layer 30, first electrode layers 21a and 21b, and a second electrode layer 22a. Below, "above" represents a direction which is separated from the substrate 60 in an ultrasonic wave emission direction and "below" represents a direction of being closer to the substrate 60 in the opposite direction to the ultrasonic wave emission direction.

The first electrode layer 21a is formed above the vibrating film 50 in a line shape along the first direction D1 (the slice direction). The second electrode layer 22a is configured by an electrode layer LCd1 which is formed above the first electrode layer 21a in a line shape along the first direction D1 and an electrode layer LCd2 which extends from the electrode layer LCd1 in the second direction D2 (the scanning direction). The electrode layer LCd2 is formed so as to cover an upper section of the piezoelectric body layer 30. The electrode layer LCd1 corresponds to one out of the signal electrode wiring and the common electrode wiring. The electrode layer LCd2 is also used as the upper electrode of the ultrasonic element, and for example, a portion which overlaps with the piezoelectric body layer 30 in the plan view in FIG. 9A is equivalent to the upper electrode.

The first electrode layer 21b is formed above the vibrating film 50 in a line shape along the first direction D1. The piezoelectric body layer 30 is provided above the opening 40 and the first electrode layer 21b is formed between the piezoelectric body layer 30 and the vibrating film 50. The first electrode layer 21b corresponds to the other out of the signal electrode wiring and the common electrode wiring. In addition, the first electrode layer 21b is also used as the lower electrode of the ultrasonic element, and for example, a portion which overlaps with the piezoelectric body layer 30 in the plan view in FIG. 9A is equivalent to the lower electrode.

In the embodiment above, the signal electrode wiring (the first electrode layer 21b) is arranged in the first direction D1 to include a position which overlaps with the piezoelectric body layer 30 (the transducer section in a broad meaning) in a plan view with respect to the ultrasonic element array 100. The common electrode wiring (the electrode layer LCd1) is arranged in the first direction D1 at a position which does not overlap with the piezoelectric body layer 30 in a plan view with respect to the ultrasonic element array 100.

According to this, it is possible to narrow the element pitch in the scanning direction (the second direction D2) since it is possible to arrange the first electrode layer 21b below the piezoelectric body layer 30. Due to this, it is possible to suppress grating lobes in the scanning direction.

Figure 10B:
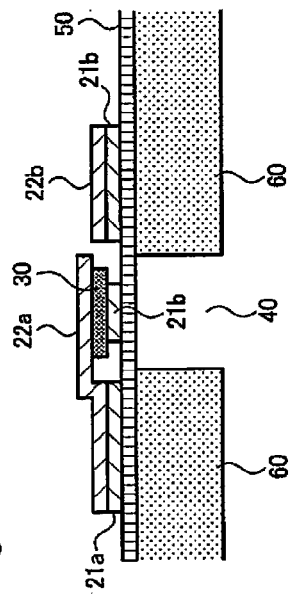
FIGS. 10A to 10C are second detailed configuration examples of an ultrasonic transducer device.
Figure 10C:
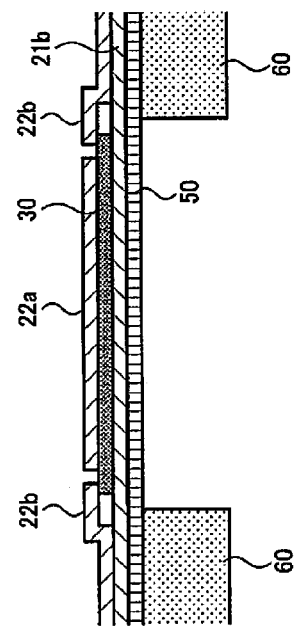
Figure 10A:
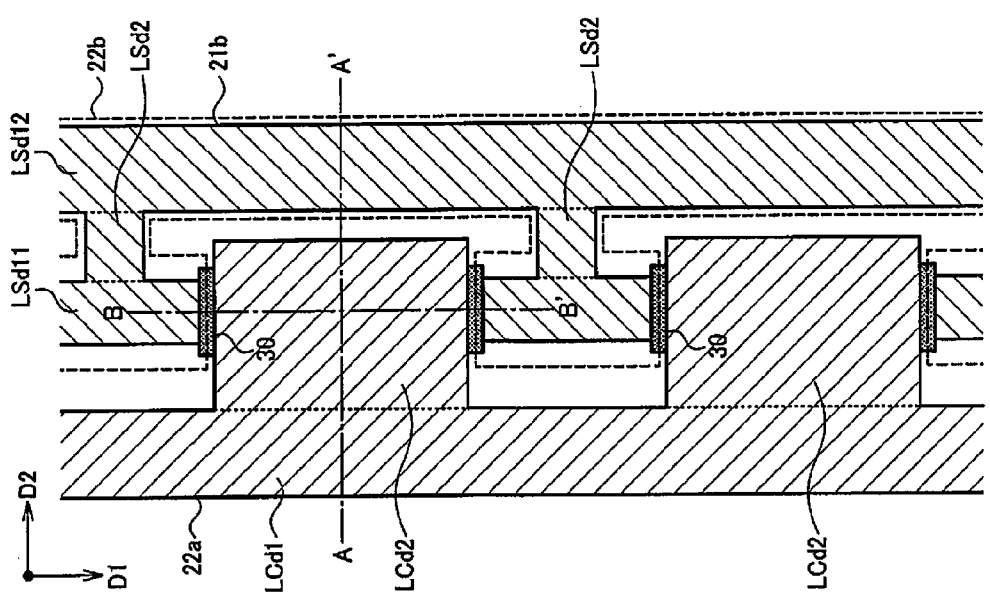

FIGS. 10A to 10C illustrate a second detailed configuration example of the ultrasonic transducer device 200. FIG. 10A is a plan view diagram with a plan view of the substrate 60, FIG. 10B is a cross sectional diagram at an AA' cross section of FIG. 10A, and FIG. 10C is a cross sectional diagram at a BB' cross section of FIG. 10A.

The ultrasonic transducer device 200 includes the substrate 60, the vibrating film 50, the piezoelectric body layer 30, the first electrode layers 21a and 21b, and second electrode layers 22a and 22b.

The configurations of the first electrode layer 21a and the second electrode layer 22a are the same as the first detail configuration example, and thus the descriptions thereof are omitted.

The first electrode layer 21b is configured by electrode layers LSd11 and LSd12 which are formed above the vibrating film 50 in a line shape along the first direction D1 and an electrode layer LSd2 which is connected with the electrode layer LSd12 by extending from the electrode layer LSd11 in the second direction D2. The electrode layer LSd12 corresponds to the other out of the signal electrode wiring and the common electrode wiring. In addition, the electrode layer LSd11 is also used as the lower electrode of the ultrasonic element, and for example, a portion which overlaps with the piezoelectric body layer 30 in the plan view in FIG. 10A is equivalent to the lower electrode. The second electrode layer 22b is formed above the first electrode layer 21b so as to cover the first electrode layer 21b.

In the embodiment above, the signal electrode wiring (the electrode layer LSd12) is arranged in the first direction D1 at a position which does not overlap with the piezoelectric body layer 30 in a plan view with respect to the ultrasonic element array 100. The common electrode wiring (the electrode layer LCd1) is arranged in the first direction D1 at a position which does not overlap with the piezoelectric body layer 30 and the signal electrode wiring (the electrode layer LSd12) in a plan view with respect to the ultrasonic element array 100.

In this manner, the width of the electrode layer LSd12 is determined without limiting the width of the piezoelectric body layer 30 and it is possible to reduce wiring impedance in the signal electrode wirings by providing the electrode layer LSd12 separately to the electrode layer LSd11 which is provided below the piezoelectric body layer 30. Due to this, it is possible to supply the common voltage (and the driving signal) to the ultrasonic elements with even lower impedance.

5. Ultrasonic Measurement Apparatus

Figure 11:
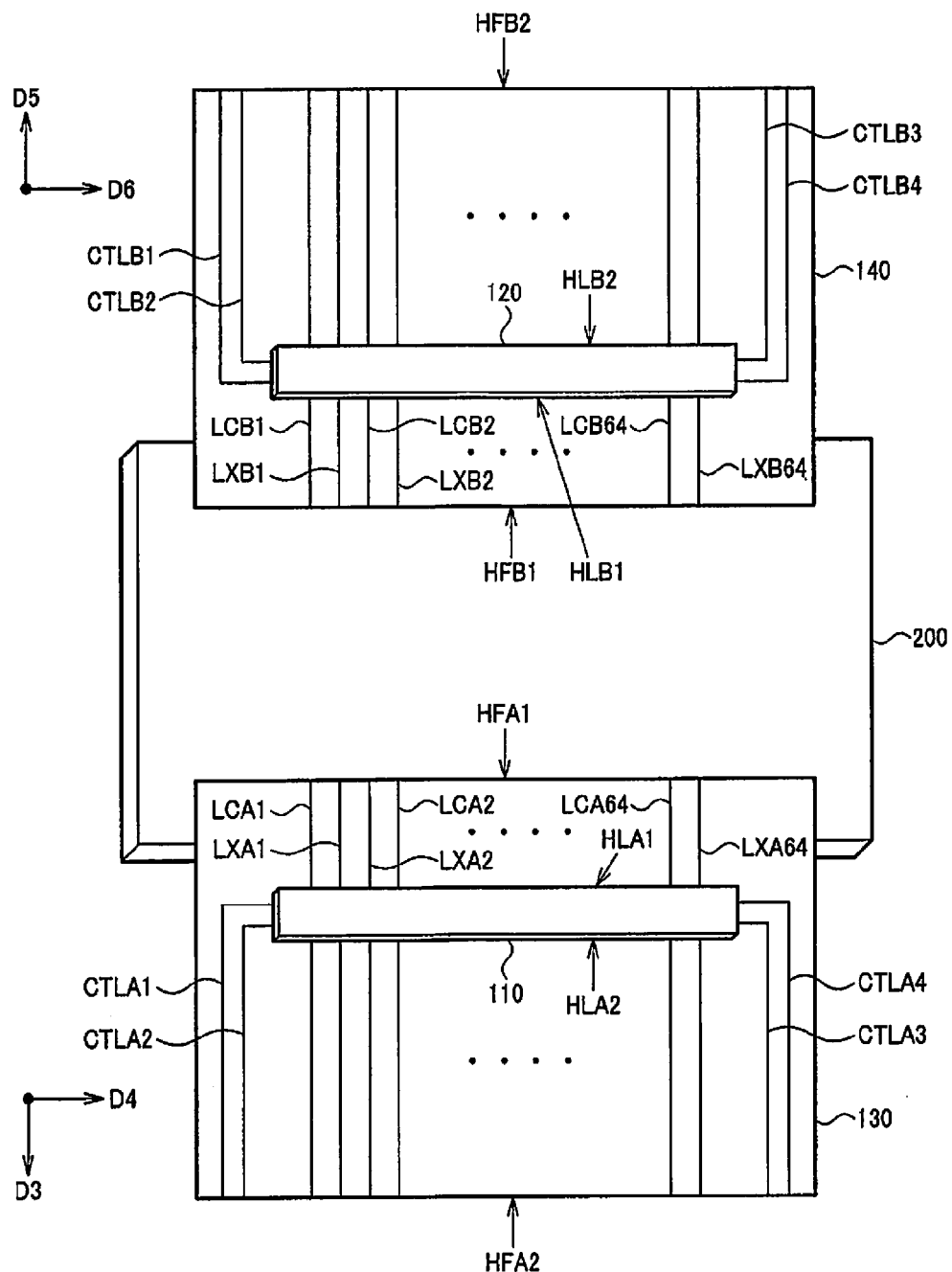
FIG. 11 is a configuration example of an ultrasonic measurement apparatus.

FIG. 11 illustrates a configuration example of the ultrasonic measurement apparatus where the ultrasonic transducer device 200 is applied. A case will be described below where an integrated circuit device which includes a transmission circuit is mounted on a flexible substrate, but the present embodiment is not limited to this and the transmission circuit may be provided on a rigid substrate in a probe.

The ultrasonic measurement apparatus includes the ultrasonic transducer device 200 (an element chip), a first flexible substrate 130, a second flexible substrate 140, a first integrated circuit device 110, and a second integrated circuit device 120. Here, the ultrasonic transducer device is also referred to as the element chip below.

As shown in FIG. 11, a direction above the flexible substrate 130 is a third direction D3 and a direction which intersects with (for example, is orthogonal to) the third direction D3 is a fourth direction D4. The flexible substrate 130 is connected with the element chip 200 at one end section HFA1 in the third direction D3 and is connected to a rigid substrate in a probe at the other end section HFA2 via, for example, a connector or the like which is not shown in the diagram. The integrated circuit device 110 is mounted to the flexible substrate 130 so that the long-side direction is along the fourth direction D4.

In detail, $1^{st}$ to $64^{th}$ signal wirings LXA1 to LXA64 and $1^{st}$ to $64^{th}$ common wirings LCA1 to LCA64 are arranged on the flexible substrate 130 along the third direction D3. One out of the ends of the $1^{st}$ to $64^{th}$ signal wirings LXA1 to LXA64 are connected with the $1^{st}$ to $64^{th}$ signal terminals XA1 to XA64 of the element chip 200, and one out of the ends of the $1^{st}$ to $64^{th}$ common wirings LCA1 to LCA64 are connected with the $1^{st}$ to $64^{th}$ common terminals CA1 to CA64 of the element chip 200. The $1^{st}$ to $64^{th}$ signal terminals XA1 to XA64 and the 1st to 64th common terminals CA1 to CA64 are formed on a surface on an ultrasonic wave emission direction side of the element chip 200 and the flexible substrate 130 is connected with the element chip 200 at the surface on the ultrasonic wave emission direction side.

The integrated circuit device 110 includes 1st to 64th transmission circuits (for example, TXA1 to TXA64 in FIG. 12) which output driving signals and 1st to 64th transmission terminals (which are not shown in the diagram) which are connected to output nodes of the 1st to 64th transmission circuits. The 1st to 64th transmission terminals are arranged along a first long side HLA1 of the integrated circuit device 110 and are respectively connected with the 1st to 64th signal wirings LXA1 to LXA64.

A common voltage output circuit which is not shown in the diagram is provided in the rigid substrate in the probe to supply the common voltage with respect to the 1st to 64th common terminals CA1 to CA64 of the element chip 200 via the 1st to 64th common wirings LCA1 to LCA64. The 1st to 64th transmissions circuits in the integrated circuit device 110 supply driving signals with respect to the 1st to 64th signal terminals XA1 to XA64 in the element chip 200 via the 1" to 64th signal wirings LXA1 to LXA64 and an ultrasonic beam is output from the element chip 200. When the element chip 200 receives an ultrasonic echo, a reception signal is output from the 1st to 64th signal terminals XA1 to XA64. A reception circuit which is not shown in the diagram is provided in the rigid substrate in the probe to receive the reception signal via the 1st to 64th signal wirings LXA1 to LXA64.

A plurality of control signal wirings CTLA1 to CTLA4 may be arranged in the flexible substrate 130. A control signal is input from, for example, a control circuit (for example, a transmitting and receiving control section 334 in FIG. 16) which is provided in the rigid substrate in the probe via the control signal wirings CTLA1 to CTLA4. For example, the control circuit outputs a control signal which instructs outputting of a driving pulse signal with respect to the transmission circuit. The control signal is output with a timing according to a delay time (output timing) of the driving pulse signal and the transmission circuit outputs the driving pulse signal at the timing of receiving the control signal.

The mounting of the integrated circuit device 110 is realized using flip-chip mounting (bare chip mounting) which uses an anisotropic conductive film (ACF). Here, flip-chip mounting is face-down mounting where, for example, the element forming surface is mounted on the flexible substrate 130 side. Alternatively, flip-chip mounting may be face-up mounting where the rear surface of the element forming surface is mounted on the flexible substrate 130 side.

In this manner, it is possible to reduce the size of the probe compared to a case where the transmission circuit is provided in the rigid substrate in the probe due to the integrated circuit device 110 which includes the transmission circuit being mounted on the flexible substrate. In addition, by performing flip-chip mounting, it is possible to reduce the mounting area compared to a case where the integrated circuit device which is a flat package is mounted on the rigid substrate. In addition, it is possible to reduce the size of the integrated circuit device 110 since it is possible for the element chip 200 of the present embodiment to be driven using approximately 10 to 30 V. As a result, it is possible to easily realize a reduction in size using flip-chip mounting which is difficult with bulk piezoelectric elements which are necessary in integrated circuit devices with high resistance to voltage.

Here, 1st to 64th dummy terminals are provided along a second long side HLA2 of the integrated circuit device 110 and the 1st to 64th dummy terminals may be connected to the 1st to 64th signal wirings LXA1 to LXA64. According to this, the force of hardening shrinkage becomes uniform at the first long side HLA1 side and the second long side HLA2 side when the terminals are conductive with the wiring due to hardening shrinkage of the anisotropic conductive film and it is possible to improve reliability of the conductivity.

It is possible to configure the second flexible substrate 140 and the second integrated circuit device 120 in the same manner as the first flexible substrate 130 and the first integrated circuit device 110. That is, 1st to 64th signal wirings LXB1 to LXB64 and 1st to 64th common wirings LCB1 to LCB64 are arranged on the flexible substrate 140 along a fifth direction D5. One out of the ends of the 1st to 64th signal wirings LXB1 to LXB64 are connected with the 1st to 64th signal terminals XB1 to XB64 of the element chip 200, and one out of the ends of the 1st to 64th common wirings LCB1 to LCB64 are connected with the 1st to 64th common terminals CB1 to CB64 of the element chip 200. The integrated circuit device 120 is flip-chip mounted on the flexible substrate 140 so that the long-side direction is along a sixth direction D6 which intersects with (for example, is orthogonal with) the fifth direction D5.

Here, a case is described in the description above where the integrated circuit devices 110 and 120 include the transmission circuits, but the present invention is not limited to this, and for example, the integrated circuit devices 110 and 120 may further include a transmission and reception switching circuit (or a limiter circuit), a multiplexer, a reception circuit, or the like.

6. Layout Configuration Example of Integrated Circuit Device

Figure 12:
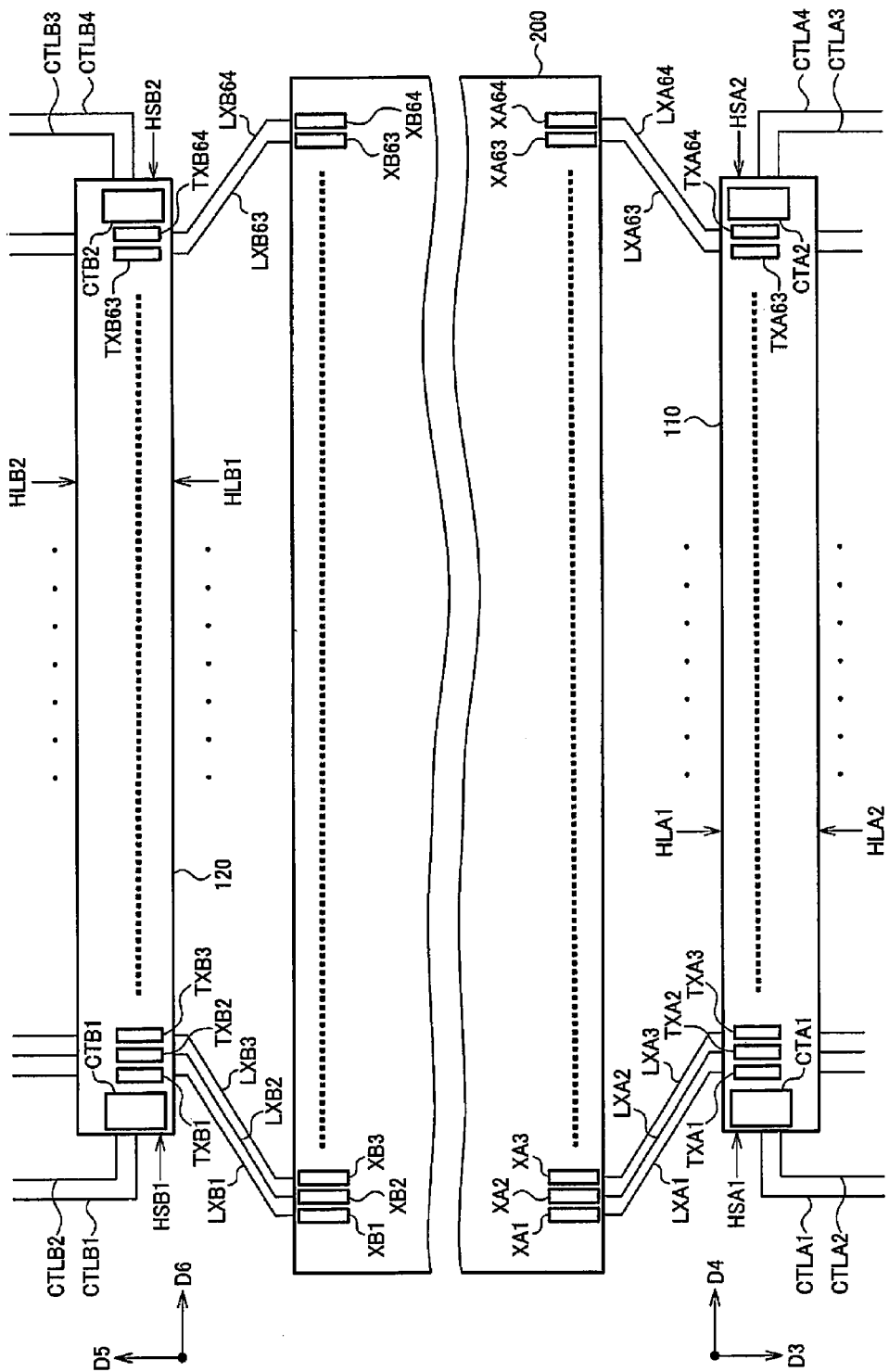
FIG. 12 is a layout configuration example of a first integrated circuit device and a second integrated circuit device.

FIG. 12 illustrates a layout configuration example of the first integrated circuit device 110 and the second integrated circuit device 120. Here, for simplicity, the common terminals CA1 to CA64 and CB1 to CB64 and the common wirings LCA1 to LCA64 and LCB1 to LCB64 are omitted from the diagram.

The integrated circuit device 110 includes the 1st to 64th transmission circuits TXA1 to TXA64 which are arranged along the fourth direction D4 (the long-side direction of the integrated circuit device 110), a first control circuit CTA1 which is arranged on a first short side HSA1 side, and a second control circuit CTA2 which is arranged on a second short side HSA2 side.

The 1st to 64th transmission circuits TXA1 to TXA64 are configured from pulsars which output driving pulse signals. The control circuits CTA1 and CTA2 are logic circuits which output control signals to the transmission circuits TXA1 to TXA64 by receiving control signals from the control circuit of the rigid substrate. Here, only one of the control circuits CTA1 and CTA2 may be included or the control circuits CTA1 and CTA2 may be omitted.

It is possible for the integrated circuit device 120 to be configured in the same manner as the integrated circuit device 110. That is, the integrated circuit device 120 includes 1st to 64th transmission circuits TXB1 to TXB64 which are arranged along the sixth direction D6 (the long-side direction of the integrated circuit device 120), a first control circuit CTB1 which is arranged on a first short side HSB1 side, and a second control circuit CTB2 which is arranged on a second short side HSB2 side.

According to the present layout configuration example, it is possible for the integrated circuit devices 110 and 120 to be configured in a long and narrow rectangular shape in the long-side direction and for the transmission circuits TXA1 to TXA64 and TXB1 to TXB64 to oppose the signal terminals XA1 to XA64 and XB1 to XB64 in the element chip 200. Due to this, it is possible for the wiring between the terminals to be simplified and for the integrated circuit devices 110 and 120 to be mounted in a compact manner with respect to the flexible substrates 130 and 140.

7. Head Unit

Figure 13:
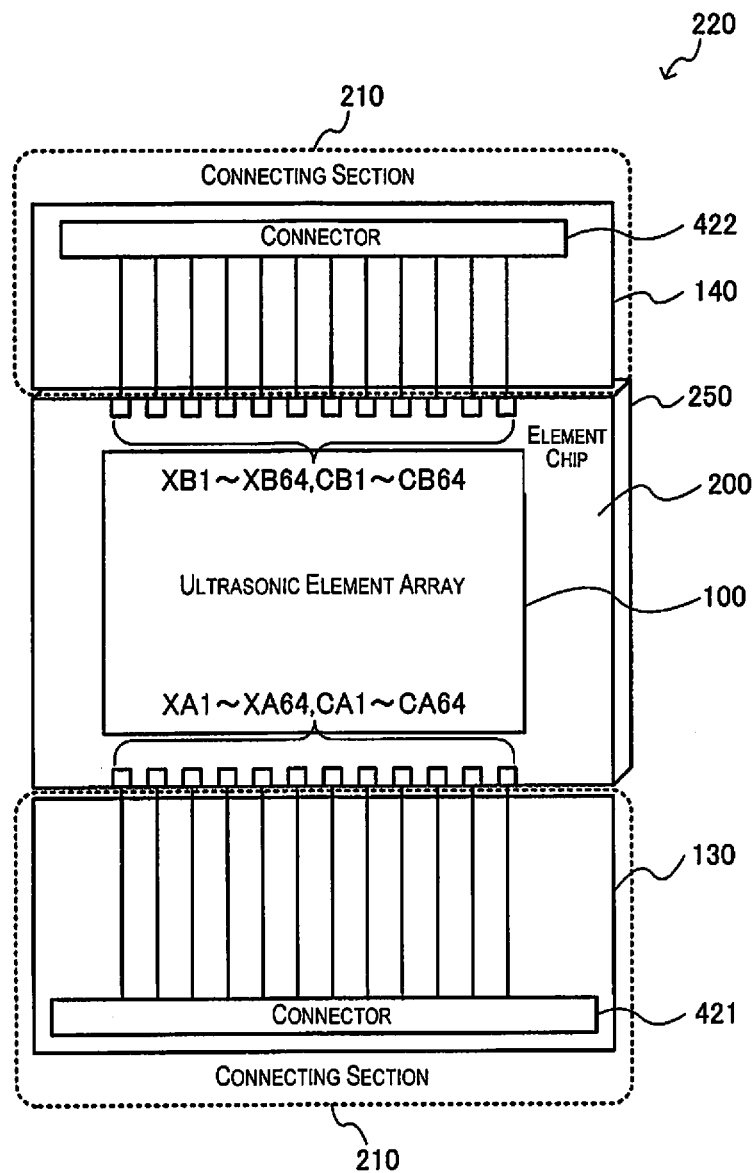
FIG. 13 is a configuration example of a head unit.

FIG. 13 illustrates a configuration example of a head unit 220 which is mounted in the ultrasonic measurement apparatus of the present embodiment. The head unit 220 shown in FIG. 13 includes the element chip 200, a connecting section 210, and a supporting member 250. Here, the head unit 220 of the present embodiment is not limited to the configuration in FIG. 13 and various modifications are possible such as a portion of the constituent elements being omitted or being replaced with other constituent elements or other constituent elements being added.

The element chip 200 includes the ultrasonic element array 100, a first chip element group (the one end side signal terminals XA1 to XA64 and the one end side common terminals CA1 to CA64), and a second chip element group (the other end side signal terminals XB1 to XB64 and the other end side common terminals CB1 to CB64). The element chip 200 is electrically connected to a processing apparatus (for example, a processing apparatus 330 in FIG. 16) which has a probe body via the connecting section 210.

The connecting section 210 electrically connects the probe body and the head unit 220 and has connectors which have a plurality of connection terminals and a flexible substrate which is formed with wiring which connects the connector and the element chip 200. In detail, the connecting section 210 has a first connector 421 and a second connector 422 as the connectors and has the first flexible substrate 130 and the second flexible substrate 140 as the flexible substrate.

A first wiring group (a plurality of signal wirings and a plurality of common wirings) which connect the first chip terminal group (XA1 to XA64 and CA1 to CA64), which are provided on a first side of the element chip 200, and a terminal group of the connector 421 is formed on the first flexible substrate 130. A second wiring group (a plurality of signal wirings and a plurality of common wirings) which connects the second chip terminal group (XB1 to XB64 and CB1 to CB64), which are provided on a second side of the element chip 200, and a terminal group of the connector 422 is formed on the second flexible substrate 140.

Here, the connecting section 210 is not limited to the configuration shown in FIG. 13, and for example, the connecting section 210 may be configured to not include the connectors 421 and 422 and may be provided with a connection terminal group instead of the connectors 421 and 422.

As above, it is possible to electrically connect the probe body and the head unit 220 by providing the connecting section 210 and it is also possible for the head unit 220 to be attached to and detached from the probe body.

FIG. 14A to FIG. 14C illustrate a detailed configuration example of the head unit 220. FIG. 14A illustrates a second surface SF2 side of the supporting member 250, FIG. 14B illustrates a first surface SF1 side of the supporting member 250, and FIG. 14C illustrates a side surface side of the supporting member 250. Here, the head unit 220 of the present embodiment is not limited to the configuration of FIG. 14A to FIG. 14C and various modifications are possible such as a portion of the constituent elements being omitted or being replaced with other constituent elements or other constituent elements being added.

The supporting member 250 is a member which supports the element chip 200. The connectors 421 and 422 (a plurality of connection terminals in a broad meaning) are provided on the first surface SF1 side of the supporting member 250. It is possible for the connectors 421 and 422 to be attached to and detached from connectors which correspond to the probe body side. The element chip 200 is supported on the second surface SF2 side which is the rear surface of the first surface SF1 of the supporting member 250. Fixing members 260 are provided at each corner section of the supporting member 250 and are used to fix the head unit 220 to a probe casing.

Here, the first surface SF1 side of the supporting member 250 is a normal direction side of the first surface SF1 of the supporting member 250, and the second surface SF2 side of the supporting member 250 is a normal direction side of the second surface SF2 which is the rear surface of the first surface SF1 of the supporting member 250.

As shown in FIG. 14C, a protective member (a protecting film) 270 which protects the element chip 200 is provided on the surface (the surface where the piezoelectric body layer 30 is formed in FIG. 1B) of the element chip 200. The protective member may also be used as an acoustic adjustment layer.

8. Ultrasonic Probe

FIG. 15A and FIG. 15B illustrate a configuration example of an ultrasonic probe 300 (a probe) where the head unit 220 described above is applied. FIG. 15A illustrates a case where a probe head 310 is mounted in a probe body 320 and FIG. 15B illustrates a case where the probe head 310 is separated from the probe body 320.

The probe head 310 includes the head unit 220 and a probe casing 240 which contains a contact member 230, which comes into contact with a subject, and the head unit 220. The element chip 200 is provided between the contact member 230 and the supporting member 250.

The probe body 320 includes the processing apparatus 330 and a probe body side connector 426. The processing apparatus 330 includes a transmission section 332, a reception section 335 (an analog front end section), and the transmission and reception control section 334. The transmission section 332 performs a process of transmitting a driving pulse (a transmission signal) to the element chip 200. The reception section 335 performs a process of receiving an ultrasonic echo signal (a reception signal) from the element chip 200. The transmission and reception control section 334 performs control of the transmission section 332 and the reception section 335. The probe body side connector 426 connects with a head unit (or probe head) side connector 425. The probe body 320 connects with an electronic device (for example, an ultrasonic imaging apparatus) body using a cable 350.

The head unit 220 is contained in the probe casing 240, but it is possible to remove the head unit 220 from the probe casing 240. By doing this, it is possible to replace only the head unit 220. Alternatively, it is possible to replace the head unit 220 in a state of being contained in the probe casing 240, that is, as the probe head 310.

9. Ultrasonic Imaging Apparatus

Figure 16:
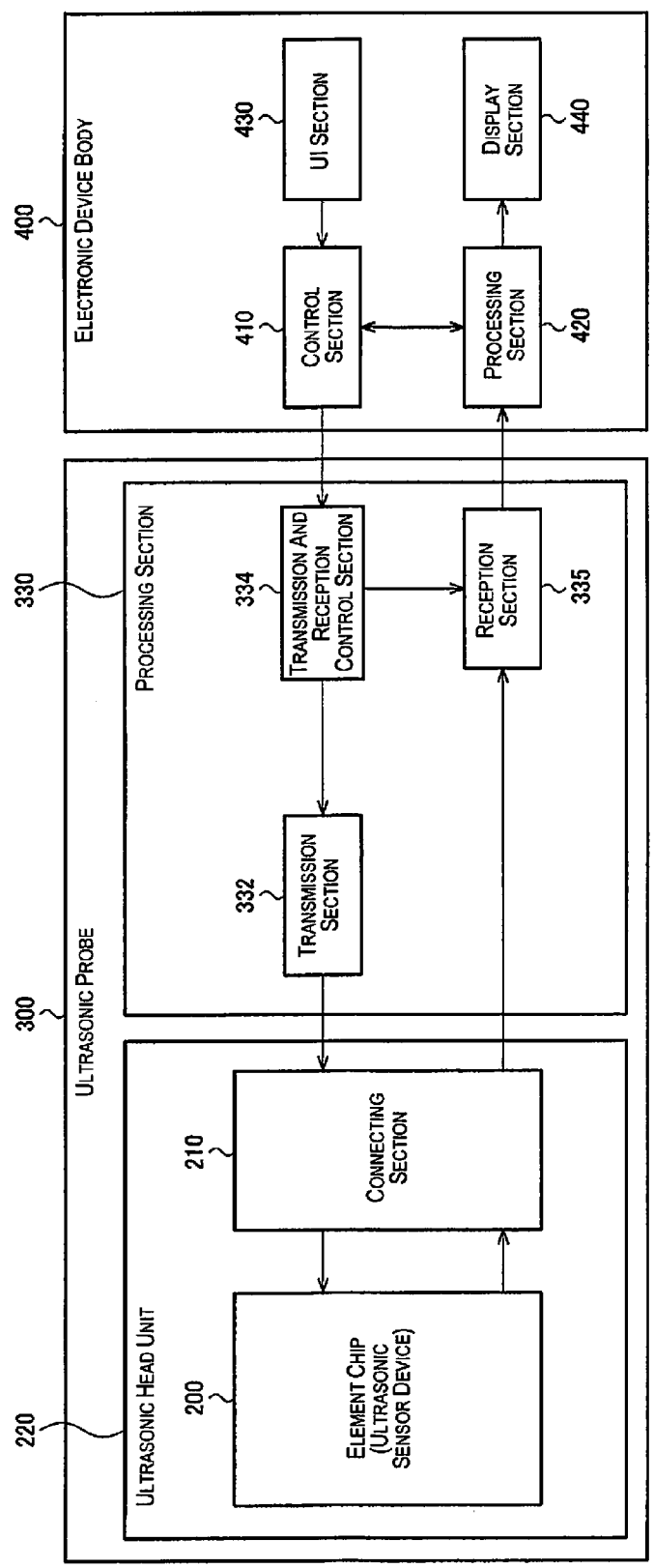
FIG. 16 is a configuration example of an ultrasonic imaging apparatus.

FIG. 16 illustrates a configuration example of an ultrasonic imaging apparatus. The ultrasonic imaging apparatus includes the ultrasonic probe 300 and an electronic device body 400. The ultrasonic probe 300 includes the head unit 220 (an ultrasonic head unit) and the processing apparatus 330. The electronic device body 400 includes a control section 410, a processing section 420, a user interface section 430, and a display section 440.

The processing apparatus 330 includes the transmission section 332, the transmission and reception control section 334, and the reception section 335 (an analog front end section). The head unit 220 includes the element chip 200 and the connecting section 210 (a connector section) which connects the element chip 200 with a circuit substrate (for example, a rigid substrate). The transmission section 332, the transmission and reception control section 334, and the reception section 335 are mounted on the circuit substrate. The transmission section 332 may include a high voltage generating circuit (for example, a booster circuit) which generates a power supply voltage of a pulsar.

In a case where ultrasonic waves are transmitted, the transmission and reception control section 334 performs a transmission instruction with respect to the transmission section 332, and the transmission section 332 receives the transmission instruction and outputs a driving voltage by amplifying a driving signal to a high voltage. In a case where reflected ultrasonic waves are received, the reception section 335 receives a reflected wave signal which is detected using the element chip 200. The reception section 335 processes the reflected wave signal (for example, an amplification process, an A/D conversion process, or the like) based on a reception instruction from the transmission and reception control section 334 and the signal after processing is transmitted to the processing section 420. The processing section 420 displays the signal on the display section 440 as an image.

Here, it is possible for the ultrasonic transducer device of the present embodiment to be applied to various electronic devices without being limited to the ultrasonic imaging apparatus for medical use as described above. For example, a diagnosis device for checking the insides of buildings and the like without damage, a user interface device which detects movement of a finger of a user using reflection of ultrasonic waves, and the like can be assumed as the electronic devices where the ultrasonic transducer device is applied.

Here, the present embodiment is described in detail as above, but it should be possible for a person skilled in the art to easily conceive that many changes are possible without substantially departing from the novel items and effects of the present invention. In accordance with this, all of the modified examples are included in the scope of the present invention. For example, in the specifications and diagrams, it is possible for terms, which are described along with different terms which have a broader or similar meaning, to be replaced at least once with the different terms in any locations in any of the specifications or diagrams. In addition, all combinations of the embodiments and modified examples are also included in the scope of the present invention. In addition, various modifications are possible with respect to the configuration and operation of the integrated circuit, the ultrasonic element, the ultrasonic transducer device, the ultrasonic measurement apparatus, the ultrasonic head unit, the ultrasonic probe, and the ultrasonic imaging apparatus, the method for mounting the integrated circuit device, and the like without being limited to what is described in the embodiments.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic transducer device comprising:
   a substrate;
   an ultrasonic element array disposed on the substrate, the ultrasonic element array having at least two ultrasonic element rows each including a plurality of ultrasonic elements arranged along a first direction, the at least two ultrasonic element rows being arranged along a second direction intersecting with the first direction;
   a signal electrode wiring disposed on the substrate, the signal electrode wiring being configured to supply or receive signals with respect to at least one of the at least two ultrasonic element rows, the signal electrode wiring having a longitudinal wiring portion extending along the first direction; and
   a common electrode wiring disposed on the substrate, the common electrode wiring being configured to supply a common voltage to the at least one of the at least two ultrasonic element rows, the common electrode wiring having a longitudinal wiring portion extending along the first direction, the common electrode wiring being arranged between the at least two ultrasonic element rows with respect to the second direction, the common electrode wiring being non-connected to the rest of the at least two ultrasonic element rows,
   wherein the ultrasonic elements of the at least one of the at least two ultrasonic element rows are electrically disposed between the signal electrode wiring and the common electrode wiring,
   the longitudinal wiring portion of the common electrode wiring does not overlap with the ultrasonic elements as viewed in a thickness direction of the substrate, with the thickness direction being a normal direction of a surface of the substrate over which the ultrasonic element array are disposed, and
   the common electrode wiring has two terminals facing each other across the ultrasonic elements.

2. The ultrasonic transducer device according to claim 1, wherein
   the ultrasonic element array has a $1^{st}$ to an $n^{th}$ ultrasonic element rows, where n is an integer of at least two or more, including the at least two ultrasonic element rows with the $1^{st}$ to the $n^{th}$ ultrasonic element rows being arranged along the second direction, and
   the common electrode wiring is configured to supply the common voltage to an $i^{th}$ to a $j^{th}$ ultrasonic element rows, where i and j are natural numbers such that i≤j≤n−1, among the $1^{st}$ to the $n^{th}$ ultrasonic element rows, and is arranged between a $k^{th}$ ultrasonic element row and a $k+1^{th}$ ultrasonic element row, where k is a natural number such that i−1≤k≤j, among an i−$1^{th}$ to the $j^{th}$ ultrasonic element rows.

3. The ultrasonic transducer device according to claim 1, wherein each of the ultrasonic elements in the at least one of the at least two ultrasonic element rows has a first electrode, a second electrode, and a transducer section arranged between the first electrode and the second electrode, with the first electrode being connected to the signal electrode wiring, and the second electrode being connected to the common electrode wiring.

4. The ultrasonic transducer device according to claim 3, wherein
the substrate has a plurality of openings arranged in an array formation, each of the ultrasonic elements has a vibrating film covering a corresponding one of the openings and a piezoelectric element section disposed on the vibrating film, and
the piezoelectric element section has a lower electrode disposed on the vibrating film as one of the first electrode and the second electrode, a piezoelectric body layer as the transducer section covering at least a portion of the lower electrode, and an upper electrode as the other of the first electrode and the second electrode covering at least a portion of the piezoelectric body layer.

5. The ultrasonic transducer device according to claim 1, further comprising:
a plurality of signal electrode wirings;
a first common electrode wiring as the common electrode wiring; and
at least a second and a third common electrode wirings,
wherein each of the signal electrode wirings extends in the first direction and configured to perform at least one of supplying and receiving of signals with respect to at least one of the ultrasonic element rows, and
each of the first to third common electrode wirings extends in the first direction and configured to supply the common voltage with respect to at least one of the ultrasonic element rows.

6. The ultrasonic transducer device according to claim 5, wherein
the first common electrode wiring is electrically connected to a $1^{st}$ to a $p^{th}$ ultrasonic element rows, where p is a natural number, among the ultrasonic element rows and is electrically not connected to a $p+1^{th}$ to a $q^{th}$ ultrasonic element rows, where q is a natural number such that q>p, among the ultrasonic element rows, and
the second common electrode wiring is electrically connected to the $p+1^{th}$ to the $q^{th}$ ultrasonic element rows and electrically not connected to the $1^{st}$ to the $p^{th}$ ultrasonic element rows.

7. The ultrasonic transducer device according to claim 5, further comprising:
a first end signal terminal arranged at a first end of the ultrasonic element array with respect to the first direction and is connected to a first end of at least one of the signal electrode wirings; and
a second end signal terminal arranged at a second end of the ultrasonic element array with respect to the first direction and is connected to a second end of the at least one of the signal electrode wirings.

8. The ultrasonic transducer device according to claim 5, further comprising:

a first end common terminal arranged at a first end of the ultrasonic element array with respect to the first direction and is connected to a first end of at least one of the first to the third common electrode wirings; and
a second end common terminal arranged at a second end of the ultrasonic element array with respect to the first direction and is connected to a second end of the at least one of the first to the third common electrode wirings.

9. The ultrasonic transducer device according to claim 5, further comprising:
a first common terminal connected with the first common electrode wiring;
a second common terminal connected with the second common electrode wiring;
a first signal terminal connected in common with a $1^{st}$ to an $r^{th}$ signal electrode wirings, where r is a natural number among the signal electrode wirings; and
a second signal terminal connected in common with a $r+1^{th}$ to a $2r^{th}$ signal electrode wirings among the signal electrode wirings,
wherein the first common electrode wiring and the $1^{st}$ to the $r^{th}$ signal electrode wirings are electrically connected to a $1^{st}$ to an $r^{th}$ ultrasonic element rows among the ultrasonic element rows, and
the second common electrode wiring and the $r+1^{th}$ to the $2r^{th}$ signal electrode wirings are electrically connected to an $r+1^{th}$ to a $2r^{th}$ ultrasonic element rows among the ultrasonic element rows.

10. The ultrasonic transducer device according to claim 3, wherein
the signal electrode wiring extends in the first direction at a position overlapping with the transducer section in a plan view with respect to the ultrasonic element arrays, and
the common electrode wiring extends in the first direction at a position which does not overlap with the transducer section in the plan view.

11. The ultrasonic transducer device according to claim 3, wherein
the signal electrode wiring extends in the first direction at a position which does not overlap with the transducer section in a plan view with respect to the ultrasonic element arrays, and
the common electrode wiring extends in the first direction at a position which does not overlap with the transducer section and the signal electrode wiring in the plan view.

12. A head unit of a probe comprising:
the ultrasonic transducer device according to claim 1,
wherein the ultrasonic transducer device is configured to be attached and detached 13. A probe comprising:
the ultrasonic transducer device according to claim 1; and
a probe body.

14. An ultrasonic imaging apparatus comprising:
the ultrasonic transducer device according to claim 1; and
a display section configured to display image data.

15. An ultrasonic transducer device comprising:
a substrate having a first surface and a second surface opposing to the first surface;
an ultrasonic element array disposed over the first surface of the substrate,
the ultrasonic element array having a plurality of ultrasonic element rows each including a plurality of ultrasonic elements arranged along a first direction, the ultrasonic element rows being arranged along a second direction intersecting with the first direction;

a plurality of signal electrode wirings arranged along the second direction over the first surface of the substrate, the signal electrode wirings having a longitudinal wiring portion extending along the first direction, the signal electrode wirings each being configured to supply or receive signals with respect to at least one of the ultrasonic element rows; and a plurality of common electrode wirings arranged along the second direction over the first surface of the substrate, the common electrode wirings having a longitudinal wiring portion extending along the first direction, the common electrode wirings each being configured to supply a common voltage to the at least one of the ultrasonic element rows, wherein the common electrode wirings are non-connected to each other in the substrate, the longitudinal wiring portions of the common electrode wirings do not overlap with the ultrasonic elements as viewed in a thickness direction of the substrate, with the thickness direction being a normal direction of the first surface of the substrate over which the ultrasonic element array are disposed, and the common electrode wirings each have two terminals facing each other across the ultrasonic elements.

16. An ultrasonic measurement apparatus comprising:
an ultrasonic transducer device including
a substrate,
an ultrasonic element array disposed on the substrate, the ultrasonic element array having at least two ultrasonic element rows each including a plurality of ultrasonic elements arranged along a first direction, the at least two ultrasonic element rows being arranged along a second direction intersecting with the first direction,
a common electrode wiring disposed on the substrate, the common electrode wiring being configured to supply a common voltage to at least one of the at least two ultrasonic element rows, the common electrode wiring having a longitudinal wiring portion extending along the first direction, the common electrode wiring being arranged between the at least two ultrasonic element rows with respect to the second direction, the common electrode wiring being non-connected to the rest of the at least two ultrasonic element rows, and
at least two signal electrode wirings disposed on the substrate, the signal electrode wiring being configured to perform at least one of supplying and receiving of signals with respect to corresponding ones of the at least two ultrasonic element rows;
a first flexible substrate including a plurality of first signal wirings; and
a second flexible substrate including a plurality of second signal wirings,
wherein the ultrasonic elements of the at least one of the at least two ultrasonic element rows are electrically disposed between at least one of the at least two signal electrode wirings and the common electrode wiring,
the longitudinal wiring portion of the common electrode wiring does not overlap with the ultrasonic elements as viewed in a thickness direction of the substrate, with the thickness direction being a normal direction of a surface of the substrate over which the ultrasonic element array are disposed,
the common electrode wiring has two terminals facing each other across the ultrasonic elements,
at least two of the first signal wirings are respectively connected to first ends of the at least two signal electrode wirings, and
at least two of the second signal wirings are respectively connected to second ends of the at least two signal electrode wirings.

17. The ultrasonic measurement apparatus according to claim 16, further comprising:
a first integrated circuit device mounted on the first flexible substrate and has a plurality of first transmission circuits; and
a second integrated circuit device mounted on the second flexible substrate and has a plurality of second transmission circuits,
wherein each of the first transmission circuits is configured to output a transmission signal to a corresponding one of the first signal wirings, and
each of the second transmission circuits is configured to output a transmission signal to a corresponding one of the second signal wirings.

* * * * *